(12) United States Patent
Merriam et al.

(10) Patent No.: US 10,674,904 B2
(45) Date of Patent: Jun. 9, 2020

(54) SYSTEMS, METHODS AND APPARATUSES FOR SUBJECTIVE SELF-REFRACTION

(71) Applicant: M.P. Optics, LLC, Buffalo, WY (US)

(72) Inventors: Ryan R. Merriam, Henrico, VA (US); Matthew A. Phares, Plano, TX (US)

(73) Assignee: M.P. Optics, LLC, Buffalo, WY (US)

( * ) Notice: Subject to any disclaimer, the term of this patent is extended or adjusted under 35 U.S.C. 154(b) by 79 days.

(21) Appl. No.: 15/705,774

(22) Filed: Sep. 15, 2017

(65) Prior Publication Data

US 2019/0082951 A1 Mar. 21, 2019

(51) Int. Cl.
| | | |
|---|---|---|
| A61B 3/02 | (2006.01) |
| A61B 3/032 | (2006.01) |
| A61B 3/00 | (2006.01) |
| A61B 3/028 | (2006.01) |

(52) U.S. Cl.
CPC ............ *A61B 3/032* (2013.01); *A61B 3/0033* (2013.01); *A61B 3/028* (2013.01)

(58) Field of Classification Search
CPC ....... A61B 3/032; A61B 3/0033; A61B 3/024; A61B 3/028
USPC ........................................................ 351/223
See application file for complete search history.

(56) References Cited

U.S. PATENT DOCUMENTS

| | | |
|---|---|---|
| 2,882,789 A | 4/1959 | Wilson |
| 4,385,813 A | 5/1983 | Klein et al. |
| 5,812,241 A | 9/1998 | Doms et al. |
| 6,923,541 B2 | 8/2005 | Hosoi et al. |
| 7,241,013 B2 | 7/2007 | Nozawa |
| 7,438,416 B2 | 10/2008 | Hayashi et al. |
| 7,874,676 B2 | 1/2011 | Hosoi |
| 8,069,060 B2 | 11/2011 | Tipirneni |
| 9,155,461 B2 | 10/2015 | Bartlett et al. |
| 9,241,621 B2 | 1/2016 | Park et al. |
| 9,280,685 B2 | 3/2016 | Jackson |

(Continued)

FOREIGN PATENT DOCUMENTS

EP 2878989 A1 6/2015

OTHER PUBLICATIONS

"International Search Report for PCT/US2018/049472 dated Nov. 14, 2018".

*Primary Examiner* — William R Alexander
*Assistant Examiner* — Henry A Duong
(74) *Attorney, Agent, or Firm* — Marin Patents, LP; Gustavo Marin

(57) ABSTRACT

The system allows one with no prior training in refraction to subjectively screen, measure, and correct for their own refractive error without the assistance of a second person through subjective self-refraction (SSR). One accomplishes SSR by interacting with refractor input controls, which manipulate lenses in front of their eye(s). The SSR process is accomplished via pre-programming, allowing for direct feedback between the system and user from sensory cues that are prompted by interacting with the input controls. The resulting health data may be displayed or transmitted to the user or another individual for later use. The refraction process may incorporate remote data management technology and computer network capabilities that provides for efficiency, improved accuracy, cost savings and user experience enhancement and may allow for greater access to vision correction services for many people.

17 Claims, 27 Drawing Sheets

(56) References Cited

U.S. PATENT DOCUMENTS

| | | |
|---|---|---|
| 9,408,533 B2 | 8/2016 | Lai et al. |
| 2008/0143961 A1 | 6/2008 | Marino et al. |
| 2008/0198328 A1 | 8/2008 | Seriani et al. |
| 2008/0284979 A1* | 11/2008 | Yee ................ A61B 3/0091 351/209 |
| 2009/0310084 A1* | 12/2009 | Foster ................ A61B 3/18 351/223 |
| 2011/0082704 A1 | 4/2011 | Blum |
| 2013/0070204 A1* | 3/2013 | Johansson ........... A61B 3/024 351/224 |
| 2014/0240655 A1* | 8/2014 | Pugh .................. G02C 7/04 351/158 |
| 2015/0150445 A1 | 6/2015 | Iravani et al. |
| 2015/0153589 A1* | 6/2015 | Meschenmoser ............... B29D 11/00028 351/159.48 |
| 2015/0305619 A1 | 10/2015 | Liang et al. |
| 2017/0000341 A1* | 1/2017 | Samec ................ A61B 3/085 |
| 2017/0079523 A1* | 3/2017 | Limon ................ A61B 3/032 |
| 2017/0100031 A1* | 4/2017 | Lai .................... A61B 3/0285 |

\* cited by examiner

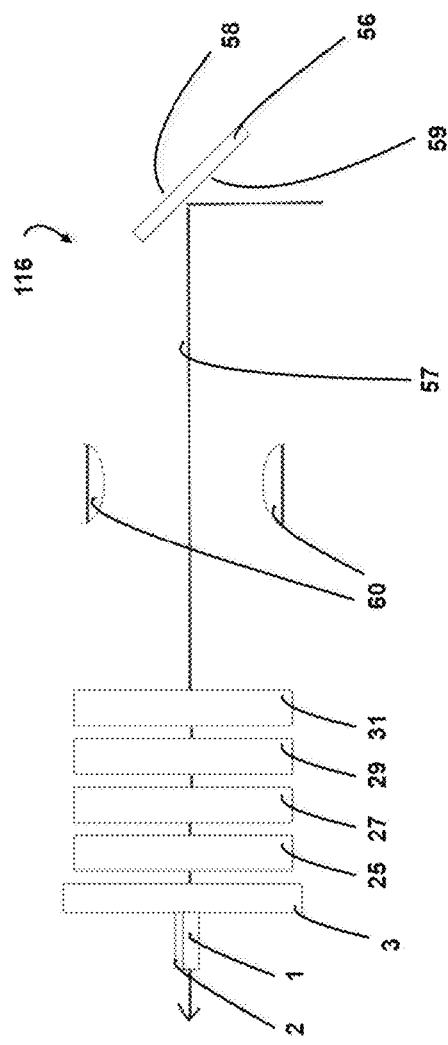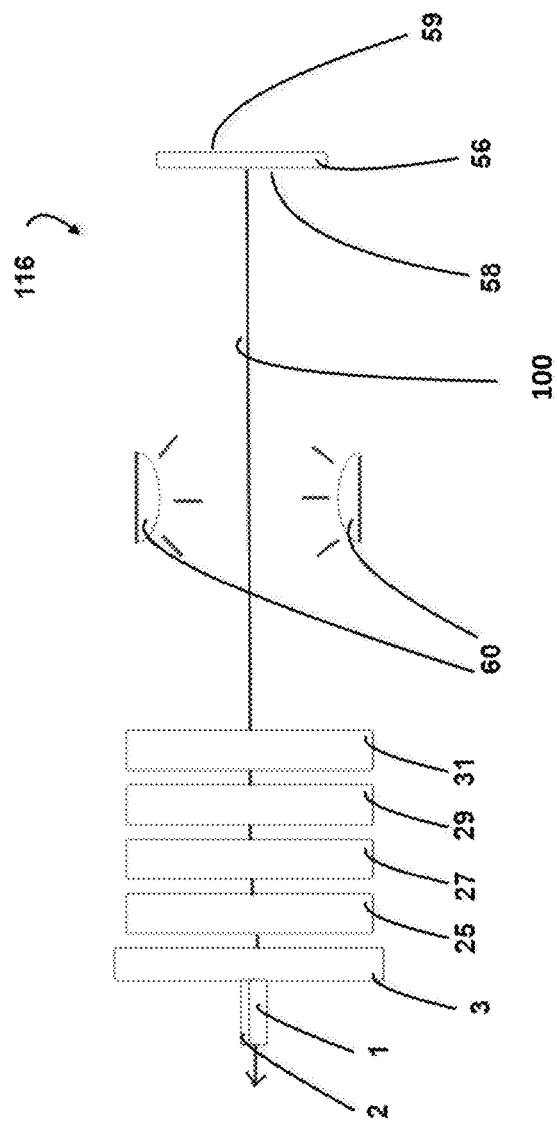
FIG. 7A
FIG. 7B

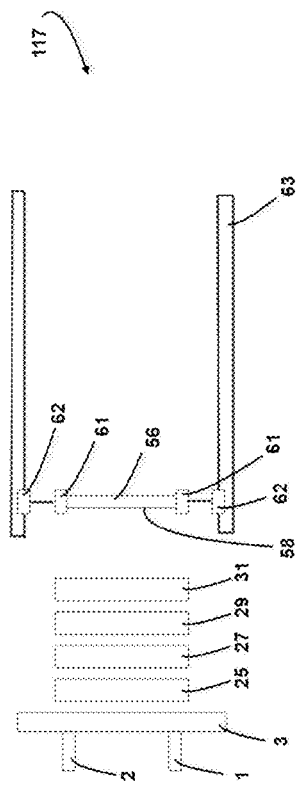
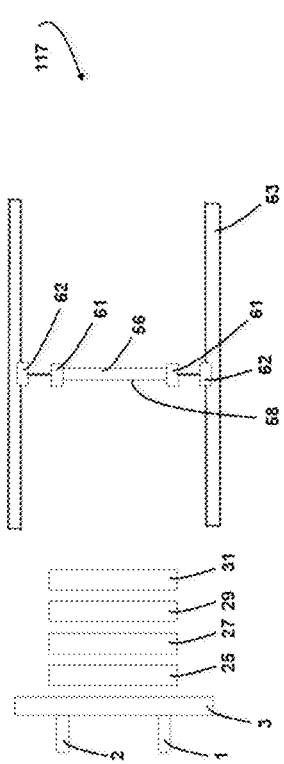
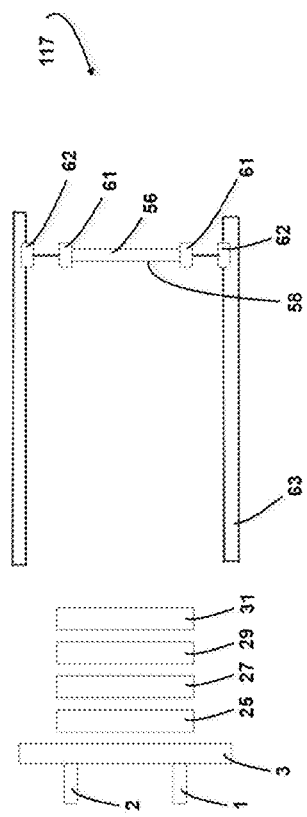
FIG. 9A
FIG. 9B
FIG. 9C

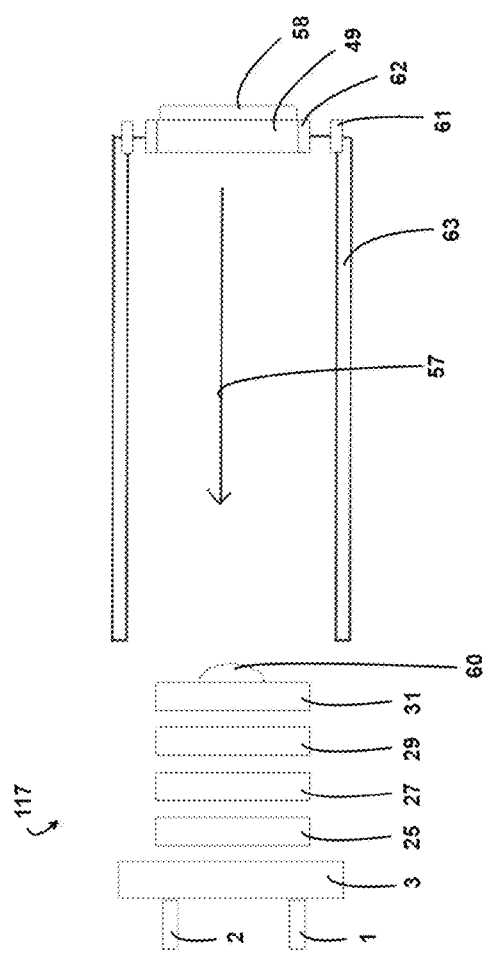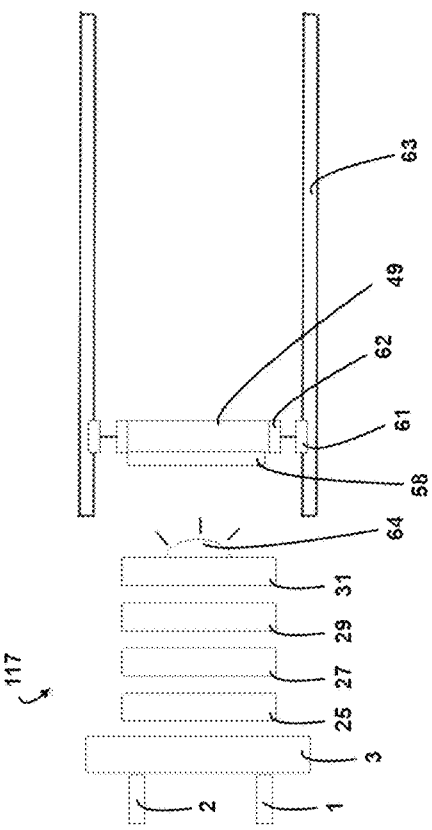
FIG. 10A
FIG. 10B

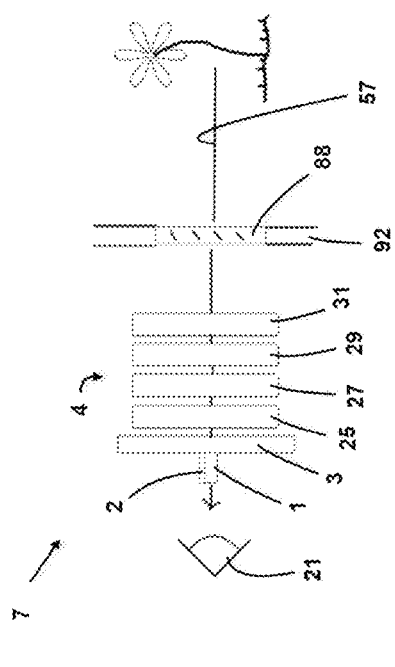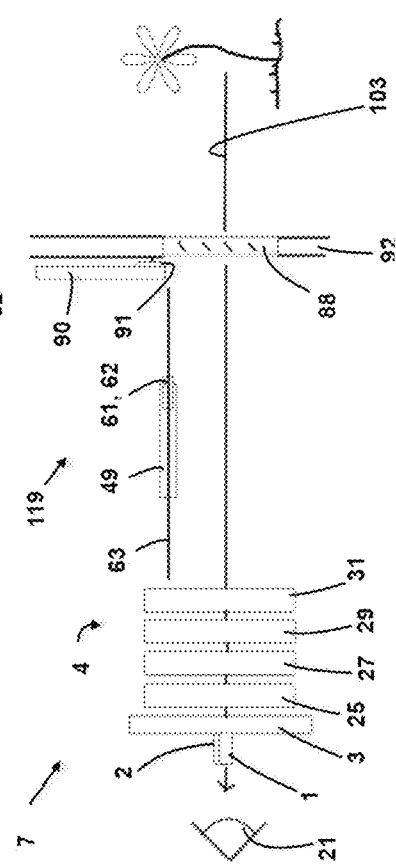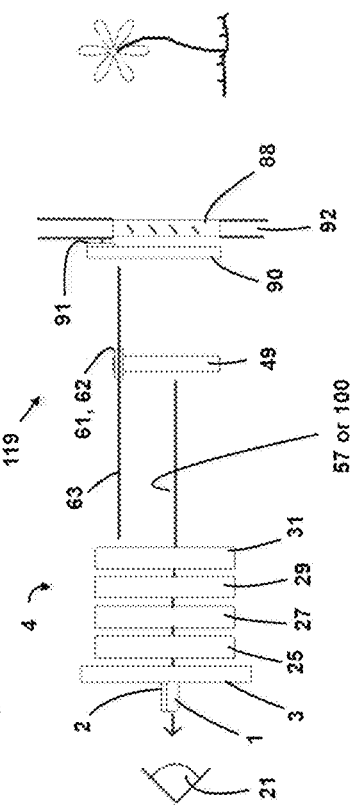

| D | | Optical Elements | | | | | | | |
|---|---|---|---|---|---|---|---|---|---|
| | | 1 | 2 | 3 | 4 | 5 | 6 | 7 | 8 |
| T | H-SPH | Plano | -2.00 | -4.00 | -6.00 | -8.00 | +2.00 | +3.00 | +4.00 |
| S | L-SPH | Plano | -0.25 | -0.50 | -.075 | +0.25 | +0.50 | +0.75 | +1.00 |
| R | H-CYL | Plano | -1.00 | -2.00 | -3.00 | | | | |
| | L-CYL | Plano | -0.25 | -0.50 | -0.75 | | | | |

FIG. 14

| Left Eye | Right Eye |
|---|---|
| Sph: | Sph: |
| Cyl: | Cyl: |
| Axis: | Axis: |
| Acuity: | Acuity: |
| Add 1: | Add 1: |
| Add 2: | Add 2: |
| Add 3: | Add 3: |
| VD: | VD: |
| PD: | PD: |

FIG. 17

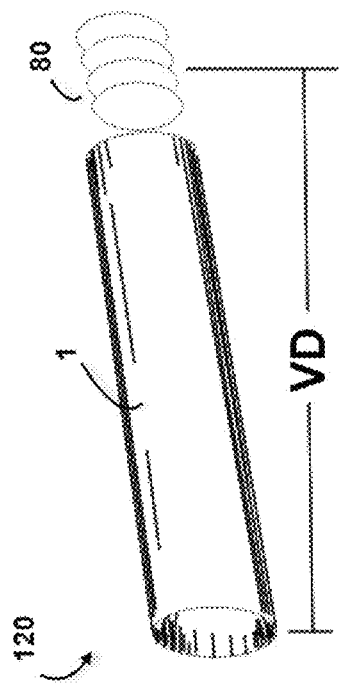
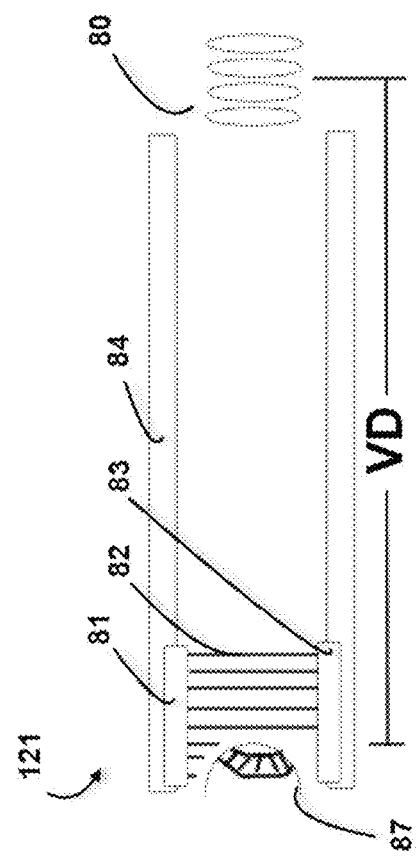
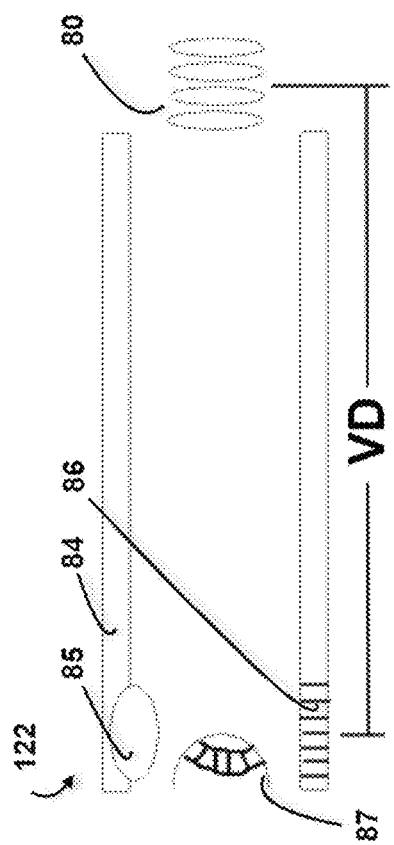

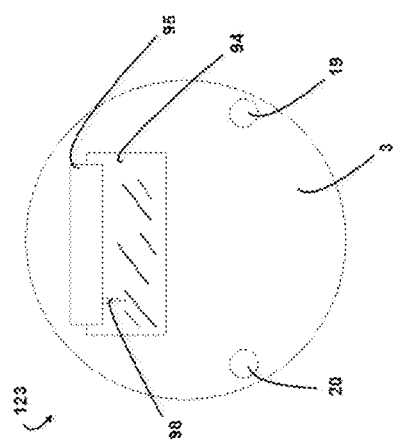
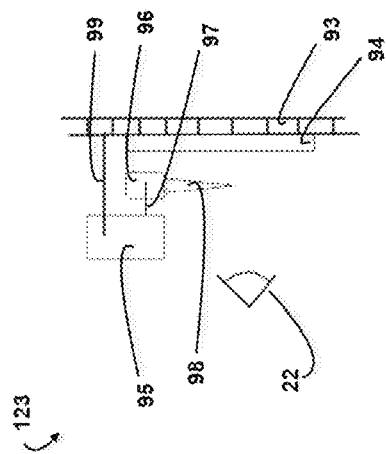
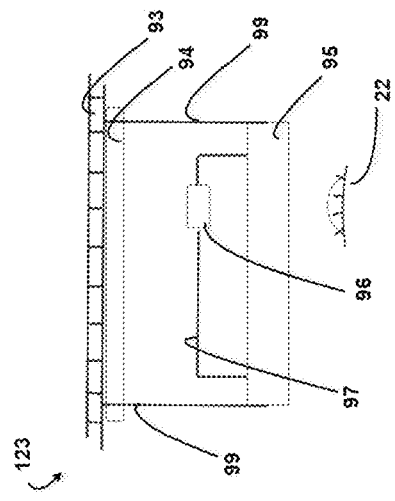
FIG. 19A
FIG. 19B
FIG. 19C

SYSTEMS, METHODS AND APPARATUSES FOR SUBJECTIVE SELF-REFRACTION

BACKGROUND

According to the world Health Organization's August 2014 update on visual impairment and blindness, uncorrected refractive errors are the main cause for moderate and severe visual impairment in the world and 80% percent of all visual impairment can be prevented or cured. Even within the U.S., many people lack the funds, insurance, or time needed for a traditional office-based refraction with an eye care professional.

Uncorrected refractive error results in loss of productivity and quality of life. More recently, objective refraction techniques have become common in the field. Objective refraction techniques attempt to correct for refractive error without a response from the user or patient. Types of objective refraction comprise: retinoscopy, auto-refractors, and wavefront aberrometers. These methods have advantages and disadvantages. A well-known problem with wavefront aberometers is that more negative diopters may be added to a prescription than is necessary causing device myopia, a condition commonly known to those skilled in the art. Retinoscopy may require a highly skilled and trained eye care professional to measure refractive error using a lens set and reflective technique but is typically not accurate enough to find the best vision. Auto-refraction, wavefront sensing and refractometers may require two people, including an eye care professional to provide instructions, read device output and troubleshoot results. They may also require sophisticated and costly equipment which places these techniques out of reach for lower income or underinsured consumers. Further, many of these devices, including auto-refractors are currently not far enough advanced to determine best vision. They are often used by eye care professionals to screen vision prior to engaging in subjective refraction, or as another benchmarking method prior to conducting surgical techniques for vision correction. When these methods are more advanced, they may replace traditional subjective methods; however, their current limitations as discussed above, are widely understood in the field and cannot find a user's preferred vision.

For years, eye care professionals have been providing patients with subjective refraction in an office based setting to correct for the above types of refractive error conditions by manipulating trial lenses by means of well-known manual and automated/motorized devices such as the phoroptor, combined with the Jackson-Cross Cylinder. Automated phoroptors are commonly used in office-based settings. It is common knowledge to those skilled in the art that these gold standard methods are the most accurate means for measuring refractive error. However, existing subjective methods may require an expert to operate or may require evaluation from an eye care professional, thus potentially impeding the possibility of a user/customer operated system.

In light of the above it would be desirable to provide an auto-phoropter system that allows a user to perform subjective self-refraction with low cost, flexibility and data access.

INCORPORATION BY REFERENCE

All publications, patents, and patent applications mentioned in this specification are herein incorporated by reference to the same extent as if each individual publication, patent, or patent application was specifically and individually indicated to be incorporated by reference.

SUMMARY

Systems, methods, and apparatus are provided for allowing a user with no prior training in the art to perform subjective self-refraction (SSR) on at least one of their eyes. Specific embodiments provide different devices that may be described as an auto-phoropter combined with pre-programming, input controls, various sensory cues, and vision tests that provide near and distant vision refraction, visual acuity assessment, visual quality assessment, refractor vertex distance (VD) and/or pupillary distance (PD) and supporting data management technologies.

The provided systems and methods relates generally to measurements of refractive error, and, more particularly to systems, methods and apparatus for SSR by the user. Refraction is the process of finding a corrective lens that can compensate for an eye that has the presence of refractive error. The scope of refractive error for purposes of describing the provided systems and methods encompasses, but is not limited to the following types: hyperopia, myopia, presbyopia, and astigmatism. The provided systems and methods increase access to vision correction services by, improving the convenience and decreasing the cost of refraction.

A stand-alone auto-phoropter system is provided that allows a user to subjectively self-refract their vision for near and/or far distances, assess their visual acuity and/or visual quality, and provide automated VD and/or PD measurements, using voice commands, sensory cues, and a handheld controller, designed specifically for self-refraction. The provided systems may provide an adapted auto-phoropter with the ability to seamlessly transition the user from an optional built-in distant vision refraction test, to an optional built-in adjustable near vision refraction test, to an optional built-in assessment for visual acuity and/or visual quality while automating and streamlining the measuring processes for assessing VD and PD. The systems, methods and apparatus are completely self-driven by the user who may not have special training or knowledge of refractive properties or processes. In the preferred embodiment a user is guided by preprogramed sensory cues, such as voice commands and/or video instructions while operating a hand-held controller. The SSR process is made possible by implementing software programs, which are combined with subjective refractive processes. At the conclusion of the SSR process, resulting measurements may be displayed or transmitted to the user by data management technologies for various other applications. For example, the resulting measurements may be used for follow-up visitation(s) with an eye care professional or for the purchase of eyewear. Eyewear as used throughout this patent includes, but not limited to eye glasses, sunglasses, contact lenses, and the like.

An improved stand-alone device and systems which incorporate the gold standard of refraction into the SSR process are provided. It may assess both visual acuity and quality; and it may measure both VD and PD. The provided systems and methods use lenses, input controls, such as a handheld controller, and sensory cues, such as interactive real-time audio and visual commands with a "go back" button on the controls that take the user back one step in the SSR process if needed in order to determine best vision. The provided systems and methods may be used in areas of high foot traffic that allow for SSR without direction from an eye care professional. The consumer may pay a usage fee but is not required to purchase the self-refracting device before performing a SSR.

Systems and method of the present disclosure provide a standardized or automated measuring system for the refractor VD. A user is provided with a VD measurement for usage in purchasing eyewear. VD is defined as the distance from the surface of the cornea to the back surface of the eyewear lens or contact lens. Refractor VD is further defined as the distance between the surface of the cornea and back surface of a trial lens commonly used in a phoropter or trial frame. In some situations, eye care professionals who refract vision using phoroptors and lens sets do not measure VD because the process can be cumbersome or inaccurate. VD is often estimated by an eye care professional to be 8 to 14 mm. This VD estimation process may lead to inaccuracies in final the prescription and problems for an optician who is fitting eyeglasses. For example, a difference of 1 mm in the vertex distance can alter the effect of the prescription by as much as 0.50 diopters, when higher diopter correction is needed. It is thus desirable to have a standardized or automated measuring system for the refractor VD.

Systems and method of the present disclosure provide a standardized or automated measuring system for measuring PD. A user may be provided with a PD measurement for usage in purchasing eyewear. PD is the distance between the centers of each pupil. Measuring PD is important to ensure that a user's eyes are properly centered behind eyewear to prevent image distortion.

Systems and method as provided herein may allow a user to find a user's best vision with improved efficiency. One or more optical elements may be manipulated and adjusted in a timely fashion according to a real-time user vision test result. The one or more optical elements may be adjusted or manipulated concurrently with a user vision test.

It is noted that there are various other embodiments of the invention and thus, the concept of SSR using a phoropter-like device, along with the systems and methods provided may undergo easy and obvious adaptations. For example, some embodiments may allow for only reading distance refraction for presbyopia, using a purely mechanical, non-electrical, non-motorized systems along with lenses of only plus diopter spherical variety along with simple written instructions for the purpose of providing the user with an accurate assessment of their appropriate reading glasses or "reader's" prescription.

In light of the above, it should be understood that the provided systems and methods may provide the user with only one or any combination of the following and in any order: SSR at one or more near distances, SSR at one or more far distances, visual acuity assessment using SSR at one or more near or far distances, visual quality assessment using SSR at one or more near or far distances, standardization or automated VD measurement(s), automated PD measurement(s), and procurement of any combination of spherical, cylindrical, axial, add, VD, or PD measurements.

In one aspect, a method for providing an automated subjective self-refraction measurement to a user is provided. The method comprises: (a) obtaining a self-vision refraction measurement from an automated self-vision test performed by the user; (b) receiving a user input indicating a desired distance for a refraction measurement; (c) configuring an optical system including adjustable corrective optics for the user to view a viewing target located at the desired distance in response to the user input and the self-vision refraction measurement; and (d) generating one or more instructions to one or more actuation units of the optical system to adjust the corrective optics in response to a user command to adjust the optical system to the automated subjective self-refraction.

In a related yet separate aspect, a system for providing an automated subjective self-refraction measurement to a user is provided. The system comprises: (i) a memory for storing a set of software instructions, and (ii) one or more processors configured to execute the set of software instructions to: (a) receive a self-vision refraction measurement from an automated self-vision test performed by the user; (b) receive a user input indicating a desired distance for a refraction measurement; (c) configure an optical system including adjustable corrective optics for the user to view a viewing target located at the desired distance in response to the user input and the self-vision refraction measurement; and (d) generate one or more instructions to one or more actuation units of the optical system to adjust the corrective optics in response to a user command to adjust the optical system to the automated subjective self-refraction.

In some embodiments, the method further comprises transmitting a refraction measurement result to a portable device. In some cases, the portable device comprises a proximity fob. In some cases, the portable device is configured to transmit the refraction measurement result to another system for automatically setting up a plurality of optics of the system according to the refraction measurement result. In some embodiments, the method further comprises transmitting an alert to a portable device. In some cases, the portable device is configured to convert an alert into a sensory cue and/or message that is picked up by the user.

In some embodiments, the automated subjective self-refraction measurement is verified by a visual stimulus and optionally wherein the visual stimulus comprises a tumbling E. In some embodiments, the self-vision test result is generated based at least in part on a percentage of graphical elements correctly identified by a user. In some cases, the self-vision test comprises a tumbling E test and a plurality of tumbling E's of the tumbling E test are oriented by the user via the user interface.

In some embodiments, the desired distance is selected from the following: a very close near vision range, a standard near vision range, a distant near vision test range, or a far vision range. In some embodiments, the viewing target is movable along a path of the optical system such that the viewing target is located at a distance corresponding to the desired distance. In some cases, the desired distance corresponds to near vision test. In some cases, a distance of the refraction measurement is adjusted to switch between a near vision test and a far vision test. In some cases, the distance is adjusted by moving one or more optical elements disposed along the optical path with aid of one or more actuators.

In some embodiments, the user command comprises increasing or decreasing an amount of optical power and wherein at least two distances corresponding to different refraction test distances have different increments of the amount of optical power. In some embodiments, the method further comprises switching to a quality test such that the user views an object in the real-world. In some cases, the viewing target is moved out of the user's viewing direction by an actuator.

In some embodiments, the automated subjective self-refraction measurement comprises a vertex distance corrected eyeglass prescription. In some embodiments, the corrective optics comprise a collimating lens.

It shall be understood that different aspects of the invention can be appreciated individually, collectively, or in combination with each other. Various aspects of the invention described herein may be applied to any of the particular applications set forth below or for any other types of the vision test system disclosed herein. Any description herein concerning the SSR measurement may apply to and be used for any other eyewear service situations. Additionally, any embodiments disclosed in the context of the SSR system are also applicable to the methods disclosed.

BRIEF DESCRIPTION OF THE DRAWINGS

The novel features of the invention are set forth with particularity in the appended claims. A better understanding of the features and advantages of the invention will be obtained by reference to the following detailed description that sets forth illustrative embodiments, in which the principles of the invention are utilized, and the accompanying drawings of which:

FIGS. 7A-B illustrate a system that allows a user to switch between distant and near vision test images in accordance with some embodiments of the invention.

FIGS. 9A-C illustrate a motorized adjusting near vision test system at three common near vision distances encountered in everyday life in accordance with some embodiments of the invention.

FIGS. 10A-B illustrate a system for testing near and far vision using a digital acuity chart with a configurable operating distance of 6 feet or less and a near vision test attached posteriorly to the digital acuity chart, which is rotatable and can be adjusted for different near distances in accordance with some embodiments of the invention. The digital acuity chart may be configured to also allow for different near vision tests at different lengths, thus making the posteriorly attached near vision test and motor gears obsolete.

FIGS. 13A-C illustrate different lens chamber systems for testing visual quality in accordance with some embodiments of the invention.

FIG. 14 illustrates the optical elements that may be found on the disks in a lens chamber in accordance with some embodiments of the invention.

FIG. 17 illustrates an example of data that may be presented on a display screen in accordance with some embodiments of the invention.

FIG. 18A-C illustrates three different automated systems for measuring the refractor VD, in accordance with some embodiments of the invention.

FIGS. 19A-C illustrates a system in accordance with some embodiments of the invention, in accordance with some embodiments of the invention.

DETAILED DESCRIPTION

Figure 1:
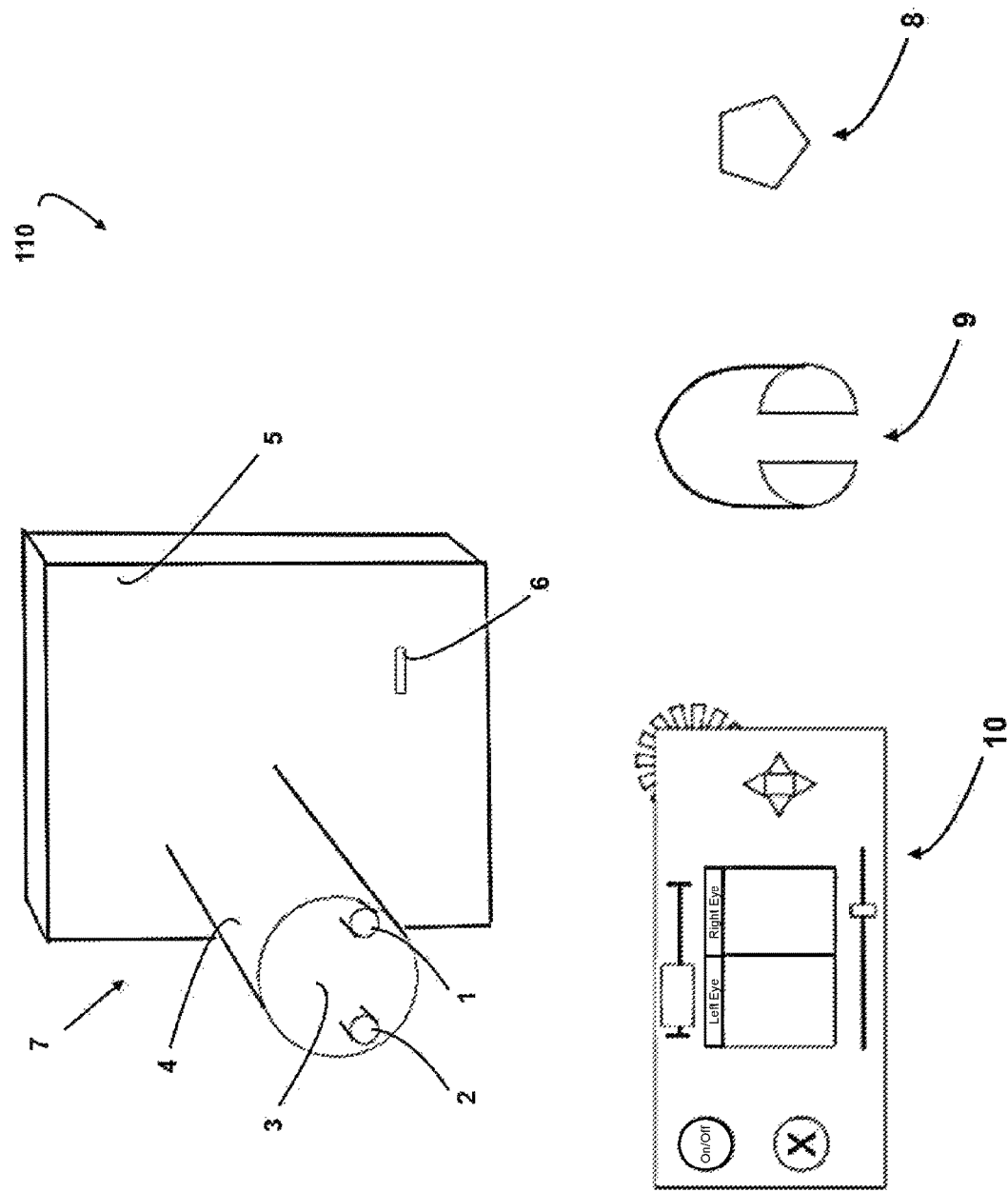
FIG. 1 illustrates a SSR system along with an optional fob device that may be used to store and transfer refractive measurements or other health data in accordance with some embodiments of the invention.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

In one aspect, an improved SSR system or apparatus is provided. The system or apparatus configured for screening and testing near and far vision, assessing visual acuity and quality by guiding a user with voice commands and/or visual instructions. The system or apparatus may automate the measuring processes for assessing VD and PD without use of the Jackson-Cross Cylinder. This provides advantages for further applications such as providing eyewear at an improved efficiency in the refractive process or lowering manufacturing costs as compared to auto-phoroptors.

In some embodiments, the systems and/or apparatus may comprise an outer casing covering a series of optical components such as lenses mounted on parallel discs. The system or apparatus may comprise user input controls, such as a controller, for controlling one or more motors to move the lenses in accordance with sensory cues, such as audio voice commands, and one or more user inputs. The system or apparatus may be configured to keep light rays focused on a user's retina when a user is performing SSR at different distances using different tests. This is advantageous to provide flexibility of the system to accommodate different users and/or uses under different conditions.

Embodiments of the invention that assess visual quality may be further adapted to allow the user to look either left or right by placing the lens chamber(s) on a motorized swivel that is controlled by the handheld controller. Benefits of this embodiment comprise further assessment of visual quality by testing the refractive measurements against real-world objects of different colors, at different angles and under different lighting conditions.

There are many other devices and mechanisms instead of an auto-phoropter, that may be used for manipulating trial lenses in front of a user's eye to accomplish SSR in combination with voice commands, eye tests, and a control unit. These devices may also be wirelessly controlled or physically attached to the hand-held controller. Thus, usage of an adapted auto-phoropter for manipulating trial lenses in front of the user's eye is the preferred method in the disclosed embodiments, but other embodiments may manipulate the trial lenses using a non-phoropter-like system.

The provided systems may also comprise an electronic media storage device with memory, which could be inserted into the hand-held controller for the purpose of saving refractive measurements. This would greatly improve the efficiency of an office-based refraction by allowing a facilitator to direct patients to take one of these memory storage devices and insert it into the controller of the system. Alternatively, the facilitator could be replaced by a set of printed, video, and/or audio instructions that directs the patient in a similar fashion. The patient would then perform SSR while waiting to see the eye care professional. Next, the patient would be directed to a same or similar system, which is operated by an eye care professional via the handheld controller. The memory storage device would be inserted into the controller and the patient would be seated at the device, viewing through the test window(s). The data saved on the storage device may then auto-manipulate the lenses in such a way that the same prescription from the waiting room refraction is in the patients optical path(s). The eye care professional may then make any necessary changes to the prescription before printing or transmitting the prescription. The patient would then take the memory storage device with him/her and drop it off with the receptionist or into a bin on their way out of the office, where data is removed from the device. Another patient can then use the same memory storage device and the process repeats itself. Efficiency may further be improved by combining proximity or contactless or wireless card or fob technology with the memory storage device. Thus, by having the patient wear the storage device as a necklace for example or place the storage device in their pocket, the patient and eye care professional may perform the above process without needing to insert and remove the memory storage device from controller. Efficiency may further be improved by adding pager technology to the memory storage device. Thus, a patient would be alerted by sensory cues emitted from the memory storage device when a refractor device becomes available in the waiting room and it is the patient's turn to use it. The memory storage device would also be able to alert the patient when it is time to go to the exam room and meet the eye care professional. Thus, the memory storage device could be adapted to serve the purpose of holding a patient's place in line. Overall, this system and method would improve patient flow during office-based refractions, improve patient experience and satisfaction, and improve the efficiency of the eye care professional's office.

FIG. 1 illustrates a SSR system 110 in accordance with some embodiments of the invention. The SSR system 110 may comprise a refractor 7, which is further comprises a lens chamber 4 and a built-in eye test. The built-in eye test may connect to, be housed within, or form part of the wall of a lens chamber 4. In the embodiment represented by FIG. 1, a mirror box 5 is used for the built-in eye test. Lens chamber 4 houses a plurality of trial lenses. Mirror box 5 houses a set of mirrors and an illuminated eye test. Lens chamber 4 may comprise a front cover 3. Attached to the front cover 3 is a left eyepiece 1 and a right eyepiece 2.

During the SSR process, light rays may be emitted from an illuminated eye test within mirror box 5, which reflect off a series of mirrors to reach optical infinity (i.e. become nearly parallel) before entering lens chamber 4. After entering lens chamber 4, the light rays are refracted by trial lenses within lens chamber 4 prior to entering the user's eye.

The lens chamber 4 may house any number of parallel disks with any number of optical elements. The embodiments provided use a High Power Spherical (H-SPH) Disk, which holds spherical lenses of high diopter (D) power, a Low Power Spherical (L-SPH) Disk which holds spherical lenses of low D power, a High Power Cylindrical (H-CYL) Disk which holds cylindrical lenses of high D power, and a Low Power Cylindrical (L-CYL) Disk which holds cylindrical lenses of low D power.

The system 110 may comprise a device or component for output of refractive measurement. The output device or component can include any hardware, software or a combination of both. For example, a printer output 6 may deliver the refractive measurements to the user. In another example, refractive measurements may be displayed on a display screen or electronically transmitted to the user through a web-based or wireless platform such as a smartphone, tablet computer or email.

The system 110 may comprise headphones 9, such as wireless headphones so the user can receive auditory instructions. The system 110 may comprise a control unit 10. The control unit 10 may comprise a mobile device such as a smartphone, tablet, iPad, notebook or other mobile device as is known to one of ordinary skill in the art. While the control unit 10 can be configured in many ways, in some embodiments the control unit 10 comprises a smartphone comprising a touch screen display, in which the touch screen display is configured to receive instructions from the user, for example. The control unit 10 may be used to manipulate the trial lenses and advance the user through the SSR process. In performing SSR, a device user follows sensory cues, such as voice commands from either headphones or speakers and provides input using a wireless or wired-in handheld controller. Instructional video may be combined with audio commands, however in the case of hearing impaired users, video instructions only may be used. Video may be available through an internet-delivery channel. It should be understood that an input controller is not always necessary to complete SSR. The user may also provide input to the device verbally via voice recognition software. At least one processor or operating unit with pre-programmed software forwards user input to at least one motor, which then drives the necessary changes in mounted lens hardware, and various systems for testing near vision, far vision, visual quality and visual acuity during the refractive process.

The system 110 may comprise a fob 8, which communicates with one or more refractor(s) 7 and electronically stores refractive measurements from the SSR process for later use. The fob can be any electronic storage unit, such as memory (e.g., read-only memory, random-access memory, flash memory) or a hard disk. The communication between the fob and the system 110 may be wireless or wired communications. The communications may include communications over a network or a direct communication. Examples of wireless communications may include, but are not limited to WiFi, 3G, 4G, LTE, radiofrequency, Bluetooth, infrared, or any other type of communications. In the case when it is a wired communication, the system 110 may comprise an interface (e.g., drivers, port) to enable the data transmission with the fob.

The fob 8 may store results of refractive testing. The resulting refractive measurements, VD and PD may be displayed, printed, or transmitted to the user or another individual for further use, such as consultations, manufacture of eyewear, and the like. For example, the refractive measurements may be used with current telehealth/telemedicine technology for the purpose of brining eye care professionals and consumers together and the like. In another example, the refractive measurements may be used for vision screening to aid a user in determining if more thorough follow-up eye care is needed. Details regarding applications of the fob are discussed later herein.

Figure 2:
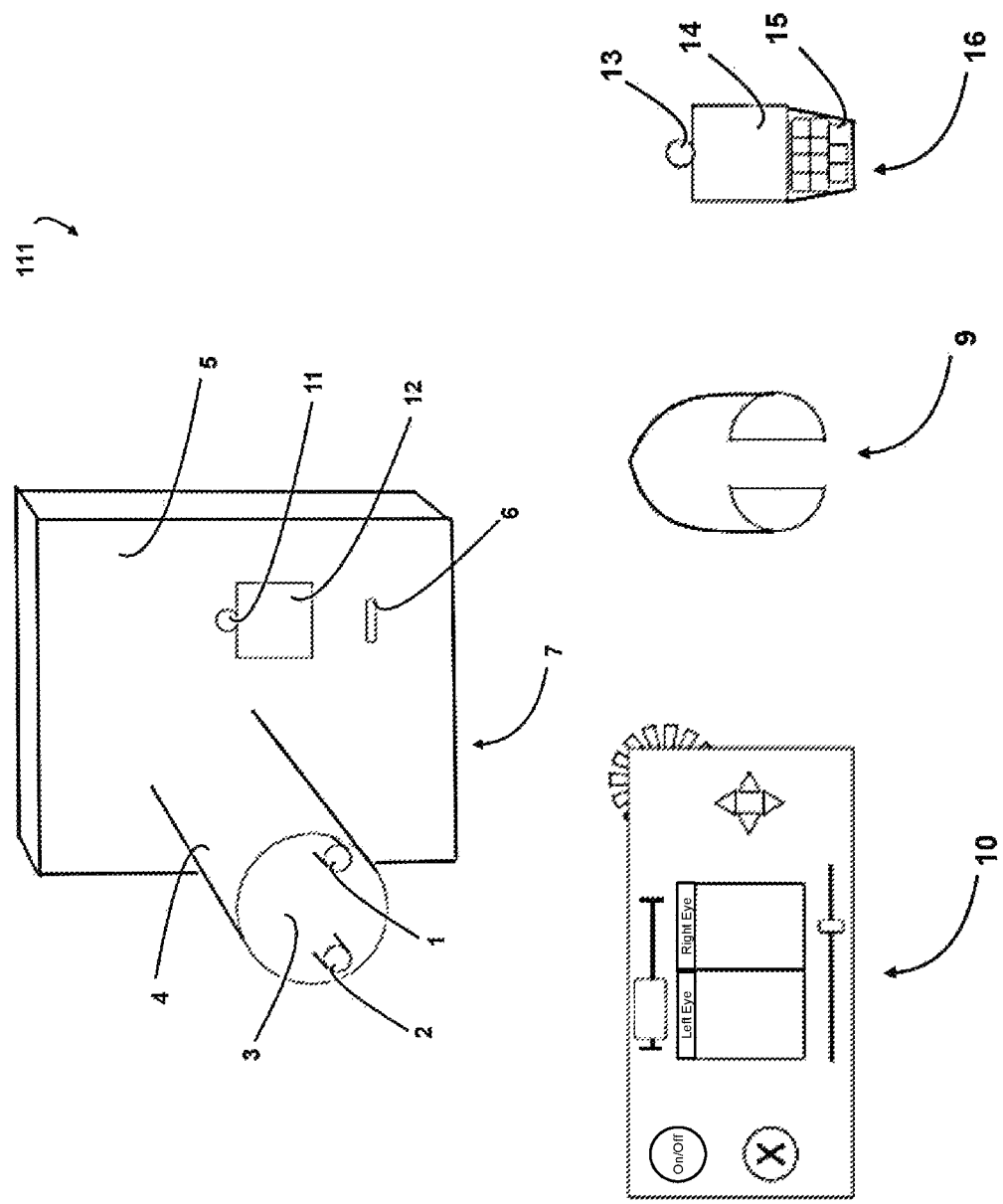
FIG. 2 illustrates a real-time audio-video portal between the user and an eye care professional in accordance with some embodiments of the invention.

In some embodiments, the SSR system may be configured to enable communication between a user and a remote eye care professional. FIG. 2 illustrates a SSR system 111 with a real-time audio-video portal between the user and an eye care professional in accordance with some embodiments of the invention. The SSR system 111 may comprise an audio-video portal that connects a user and an eye care professional in real time so they can exchange information. The audio-video portal comprises a user video camera 11, and a user video monitor 12, so that the eye care professional can interface and communicate with the device user to confirm the results of the SSR, or provide other telehealth care as necessary. Similarly, an eye care professional may use a remote eye care professional portal 16 to communicate with a user and send prescriptions. The remote eye care professional portal 16 may be located remote to the audio-video portal. Eye care professional portal 16 may comprise an eye care professional camera 13, an eye care professional video monitor 14 and an eye care professional user interactive device 15 (e.g., keyboard, button, mouse, touchscreen, touchpad, joystick, trackball). The communication may be wired or wireless communication. In some embodiments, the remote eye care professional portal may be hosted on eye care professional device. The device may be a network device capable of connecting to a network, such as a local area network (LAN), wide area network (WAN) such as the Internet, a telecommunications network, a data network, or any other type of network. The device may be capable of direct or indirect wireless communications. The device may be capable of peer-to-peer (P2P) communications and/or communications with cloud-based infrastructure. The device may be a mobile device (e.g., smartphone, tablet, pager, personal digital assistant (PDA)), a computer (e.g., laptop computer, desktop computer, server) or any other type of device. Communication may be via an internet connection or other means of remote data transmission.

Figure 3:
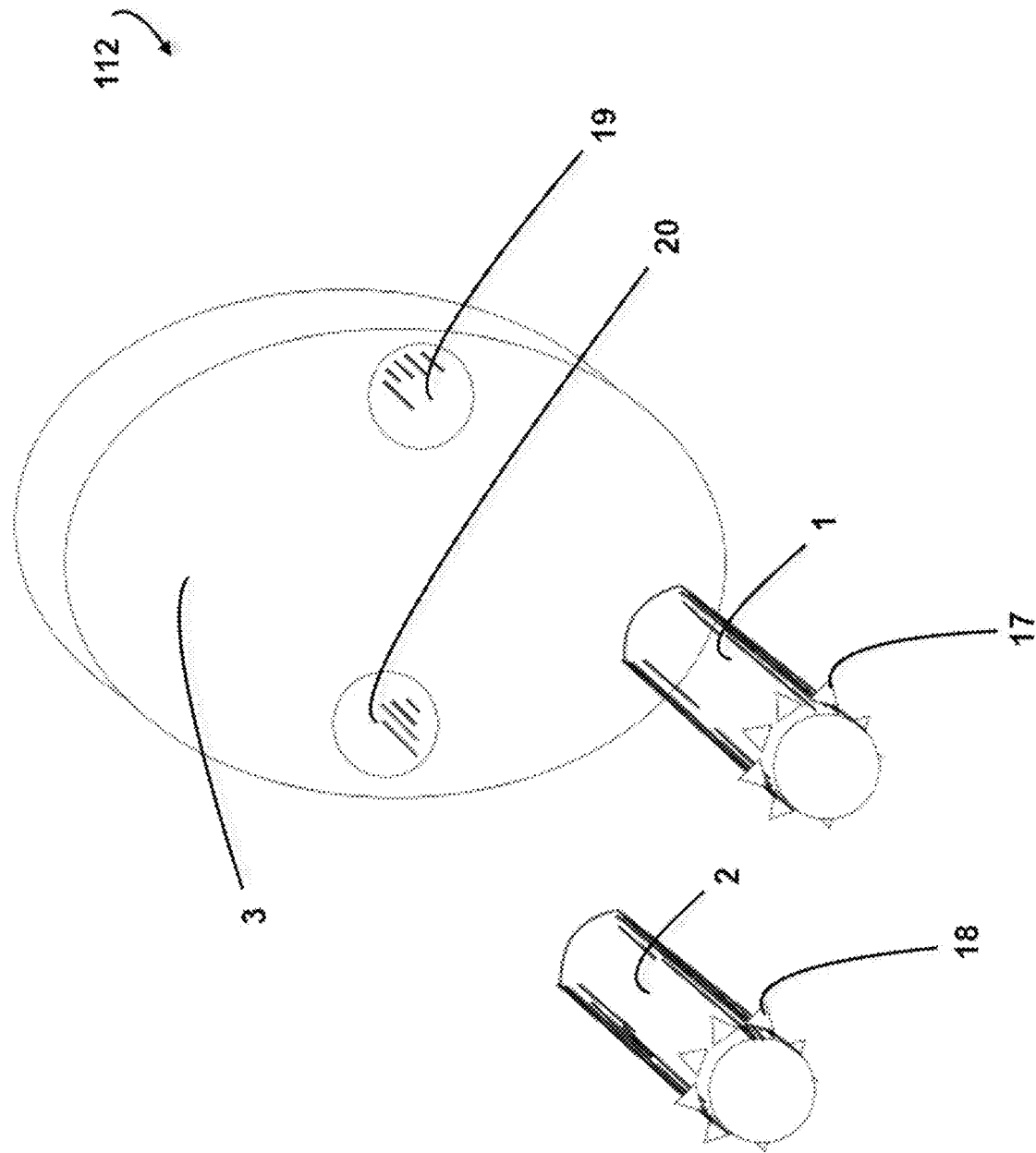
FIG. 3 illustrates a system for standardizing the VD distance using premeasured eyepieces and for ensuring correct left/right eye laterality using light signals in accordance with some embodiments of the invention.

The SSR system may comprise components for performing VD measurement. FIG. 3 is an exploded view of a system 112 for standardizing the VD distance, in accordance with some embodiments of the invention. The system 112 may comprise pre-measured eyepieces for ensuring correct left/right laterality using light signals. The system 112 may comprise a left test window 19 and a right test window 20, which are mounted to a front cover 3. Left eyepiece 1 and right eyepiece 2 are mounted directly over the left test window 19 and the right test window 20, respectively. Left eyepiece lights 17 and right eyepiece lights 18 are attached to left eyepiece 1 and right eyepiece 2, respectively. In the cases, the eyepiece lights may comprise light sources such as LED that may flash when the voice commands instruct the user to switch eyes. The lights may be turned off AFTER the user's eye is docked or may flash for just a few seconds. This is advantageous to ensure the patient looks into the correct hole and the correct prescription is provided for that eye, regardless if the user knows their right from their left. The user's end of each eyepiece is at a pre-measured and fixed position from the trial lenses, which allows for an automated and standardized measurement of VD. The eyepiece lights are preprogrammed to signal to the user, such as by flashing for example, when to look into the correct test window during SSR. This ensures that the refractive measurements are recorded for the correct eye.

In some embodiments, a disk with a collimating lens and/or a Plano lens may be added to the row of disks in the lens chamber on the side furthest from the user's eye. This collimating disk may be used to further compress the refraction distance for optical infinity for the purpose of making the device smaller. The Plano lens may be added for the purpose of switching between distance refraction and near refraction.

When looking into the device, a spherical component and/or a cylindrical component is provided. The spherical component may comprise the D sum of the spherical lenses on the H-SPH Disk and the L-SPH Disk that is in the optical path. The cylindrical component may comprise the D sum of the cylindrical lens on the H-CYL Disk and the L-CYL Disk that is in the user's optical path. In some cases, lenses of 0.25 D increments may be used, however larger or smaller D increments may be used for any number of reasons such as to lower unit cost, alter unit size, improve unit accuracy, or change the scope of refractive ailments being assessed. Astigmatism, hyperopia, myopia, and/or presbyopia and the like may or may not be tested.

Figure 4:
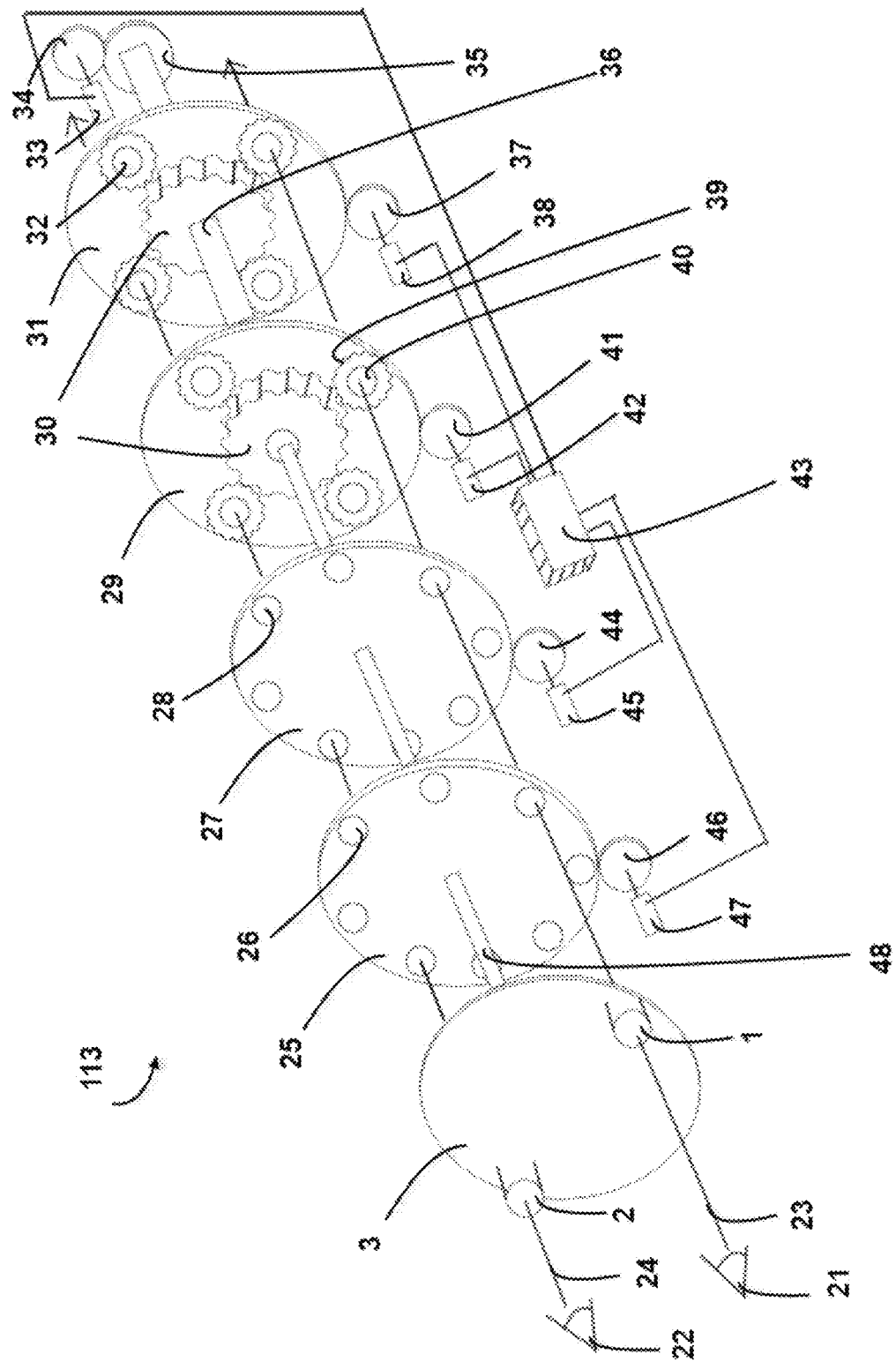
FIG. 4 is a perspective view of the front cover and internal components of a lens chamber in accordance with some embodiments of the invention.

FIG. 4 is a perspective view of a front cover 3 and the internal components 113 of a lens chamber in accordance with some embodiments of the invention. The internal components 113 consist of a series of parallel lens disks, each with mounted spherical or cylindrical lens. Variations of phoropters and vision testers; such as those described in U.S. Pat. Nos. 4,385,813 and 5,812,241, the full disclosure of which is incorporated herein by reference, are commonly known to those skilled in the art and include different lens chamber embodiments. Possibilities for lens chamber embodiments are limitless depending on the type and severity of the refractive error conditions being diagnosed or screened. The internal components 113 may comprise a high spherical power (H-SPH) disk 25 with its mounted H-SPH lenses 26; a low spherical power (L-SPH) disk 27 with its mounted L-SPH lenses 28; a high cylindrical power (H-CYL) disk 29 with each of its H-CYL lenses 40 mounted via planet gear cylindrical lens supports 39; a low cylindrical power (L-CYL) disk 31 with each of its L-CYL lenses 32 also mounted via planet gear cylindrical lens supports 39.

The internal components 113 may comprise a common shaft 48 and a hollow shaft 36. The hollow shaft 36 fits around and rotates on the axis of common shaft 48. H-SPH disk 25 and L-SPH disk 27 are suspended by and rotate around the common shaft 48. H-CYL disk 29 and L-CYL disk 31 are suspended by and rotate around the hollow shaft 36. Common shaft 48 and hollow shaft 36 rotate independent of one another and in either direction.

In some embodiments, cylindrical axis may be automatically adjusted by one or more actuators and mechanical mechanisms. Any suitable mechanical mechanism may be utilized. For example, toothed sun gears 30 and hollow shaft disk 35 are both fixed to and in phase with hollow shaft 36. Thus, power from sun gear motor 33 drives a sun gear pinion 34, allowing for rotation of the sun gears 30. Rotation of sun gears 30 cause rotation of the planet gear cylindrical lens supports 39 in the opposite direction. One or more instructions may be generated by a controller and supplied to the one or more actuators for controlling the rotational movement of the H-CYL disk. This particular embodiment allows a user to change the cylindrical axis, though other embodiments may achieve manipulation of the cylindrical axis by different means.

The internal components 113 may comprise one or more actuation units for driving a rotational movement of the H-SPH disk 25, L-SPH disk 27, H-CYL disk 29 and L-CYL disk 31. The actuation unit may comprise an actuator such as a motor and/or mechanical mechanisms. The actuators can each apply a torque to rotate the respective disk about the axis of rotation. Each actuator can be a motor including a rotor and a stator. For example, motor 47 and pinion 46; motor 45 and pinion 44; motor 42 and pinion 41; and motor 38 and pinion 37; which drive rotation of disks 25, 27, 29, and 31, respectively.

The one or more disks may be rotated in either a clockwise direction or a counterclockwise direction, or be revolved in either direction. Based on the input command, one or more processors can determine an output torque to be applied to the disk in order to achieve the desired position. The output torque can be determined in a variety of ways, such as using a controller 43. Operating unit and processor 43 interfaces with the device controller and provides the electrical input controls for all motors. For example, motors 47 and 45 may cause H-SPH lenses 26 and L-SPH lenses 28 respectively to rotate into either the left optical path 23 or the right optical path 24. Similarly, motors 42 and 38 may cause H-CYL lenses 40 and L-CYL lenses 32 to revolve in either direction around the sun gears in such a way that the orientation of the axis of each cylindrical lens is the same as each lens passes in front of either the left eye 21 or the right eye 22. In another example, motor 33 may cause rotation in either direction of the cylindrical lenses while they are in front of either eye.

In other embodiments, SSR may be achieved using two parallel lens chambers, each with one eyepiece, similar to a conventional auto-phoropter as described in U.S. Pat. No. 7,874,676 the full reference of which is incorporated herein.

Figure 5:
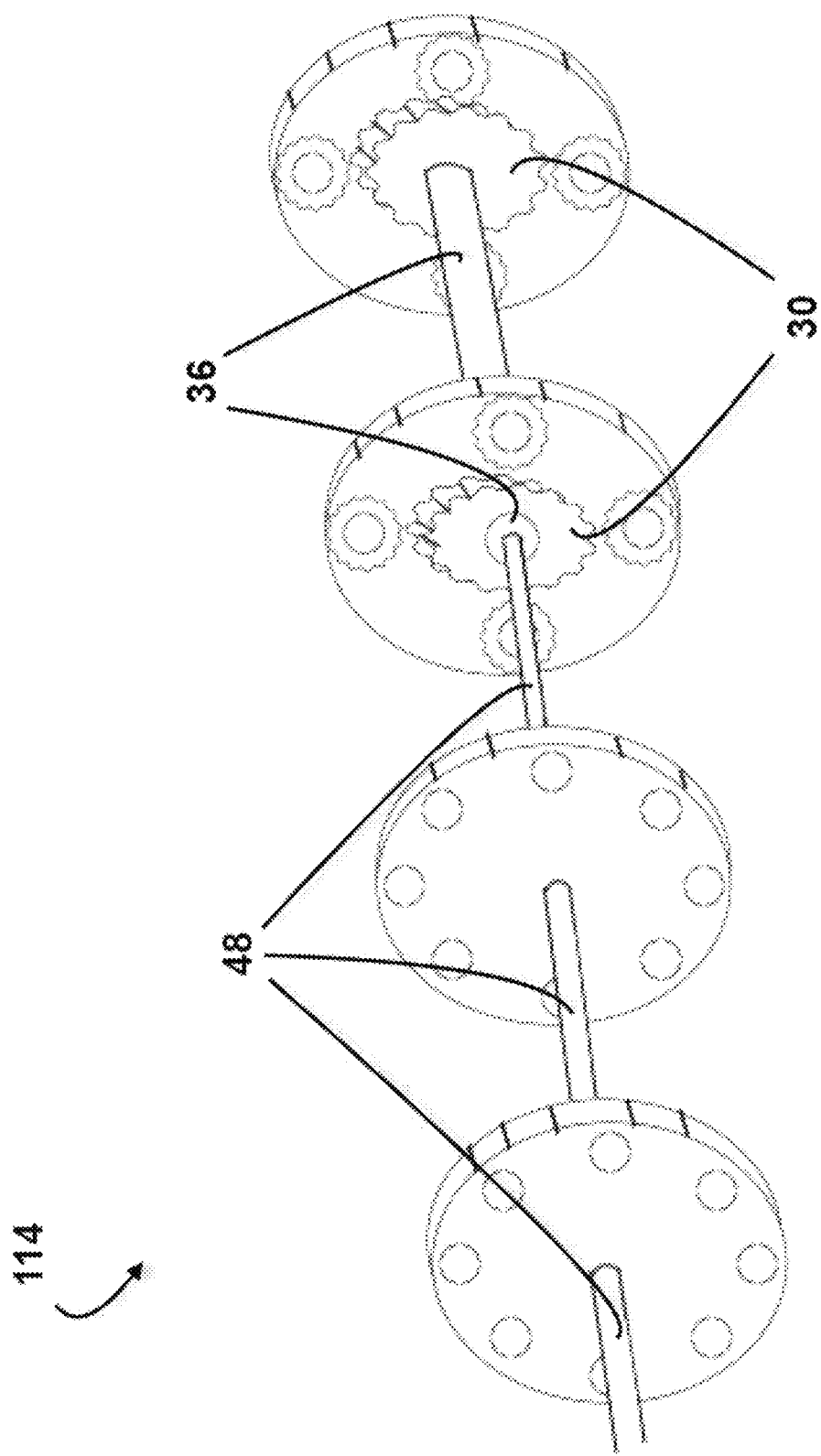
FIG. 5 is a perspective view of internal components of a lens chamber with focus on a linked sun gear mechanism for changing and retaining the cylindrical axis in accordance with some embodiments of the invention.

FIG. 5 is a perspective view of the internal components comprising a linked sun gear mechanism 114 for changing and/or retaining an axis of the cylindrical component during SSR process in accordance with some embodiments of the invention. A linked sun gear mechanism 114 may comprise one or more sun gears 30 which are affixed to and in phase with a hollow shaft 36. In some cases, the hollow shaft 36 may have a relative rotational movement about a common shaft 48. The linked sun gear mechanism 114 may be used to subjectively self-refract for astigmatism. The sun gear mechanism 114 may comprise a single sun gear. The sun gear mechanism may comprise multiple sun gears linked together such that the multiple sun gears are collectively effecting an adjustment of SSR astigmatism. Alternatively, the sun gear mechanism 114 may comprise multiple sun gears rotatable independent of each other. The linked sun gear mechanism may allow a user to change the axis of the cylindrical trial lenses in their optical path. In other embodiments that do not subjectively self-refract for astigmatism, the linked sun gear mechanism may not be necessary.

Figure 6:
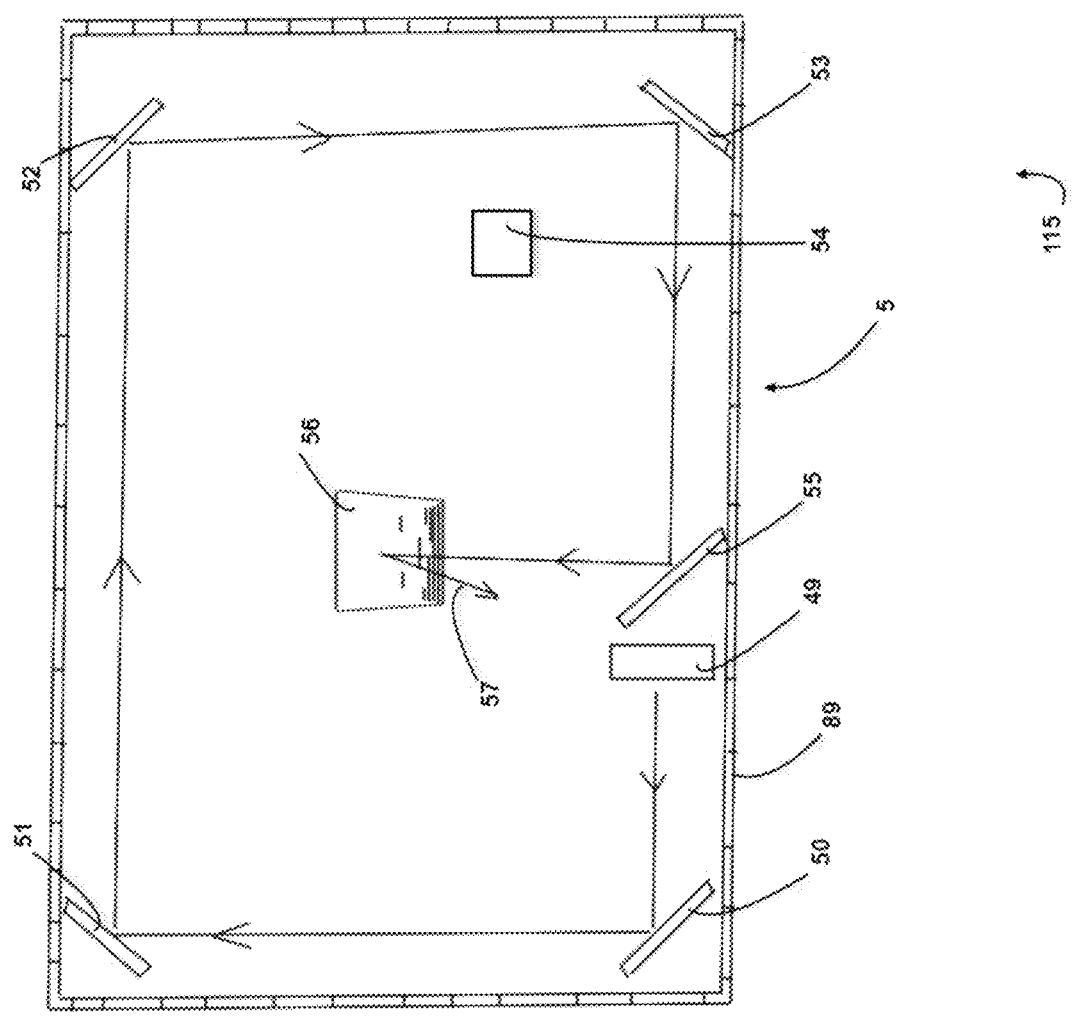
FIG. 6 illustrates a system for creating optical infinity within a compressed space in accordance with some embodiments of the invention.

FIG. 6 illustrates a system 115 for creating optical infinity within a compressed space in accordance with some embodiments of the invention. The system 115 may comprise a mirror box 5. For illustrative purposes, the mirror box 5 has a wall 89. The mirror box 5 may house a digital acuity chart 49. In this embodiment, a digital acuity chart 49 is used for the eye test, however the invention may use any type of eye test such as an illuminated image. A plurality of mirrors may be used to affect an optical path such that the digital acuity chart can be used for testing far vision, near vision and various other vision test. For example, during the SSR process, light rays 57 are emitted from a digital acuity chart 49, which sequentially reflect off a series of mirrors 50, 51, 52, 53, 55, and a rotating mirror 56. The mirrors are specifically spaced and positioned so that the light rays 57 have traveled at least 20 feet or 6 meters which is the standard distance used to represent optical infinity when testing far vision. After leaving mirror box 5, the light rays 57 are refracted by the trial lenses in lens chamber 4 prior to entering the user's eye(s). In some cases, a printer 54 may be housed in the mirror box 5 for printing refractive measurements. Alternatively, the printer 54 may be external to the mirror box 5.

FIG. 7A and FIG. 7B illustrate a system 116 that allows a user to switch between distant and near vision tests in accordance with some embodiments of the invention. The system 116 may comprise near vision test light source 60 and a rotating mirror 56. The rotating mirror 56 may have a reflective surface 59 and a near vision test chart 58 on the opposite surface.

FIG. 7A shows a system 116 in a distant vision-testing configuration wherein a rotating mirror 56 is rotated into a position, which allows for reflective surface 59 to reflect optical infinity light rays 57 through trial lenses mounted on optical disks 31, 29, 27 and 25 prior to reaching a user's eye(s). In this configuration, the near vision test light source 60 is turned off.

FIG. 7B shows a system 116 in a near vision-testing configuration wherein near vision test light source 60 may emit near vision test light rays 100, which are reflected off a near vision test chart 58. The light rays 100 travel through trial lenses mounted on optical disks 31, 29, 27 and 25 prior to reaching the user's eye(s).

In one embodiment, system 116 may be combined with a mirror box 5 and a lens chamber 4, using a rotating mirror 56 with a near vision test chart 58 affixed to one side in order to switch between distant and near vision refraction tests.

Figure 8:
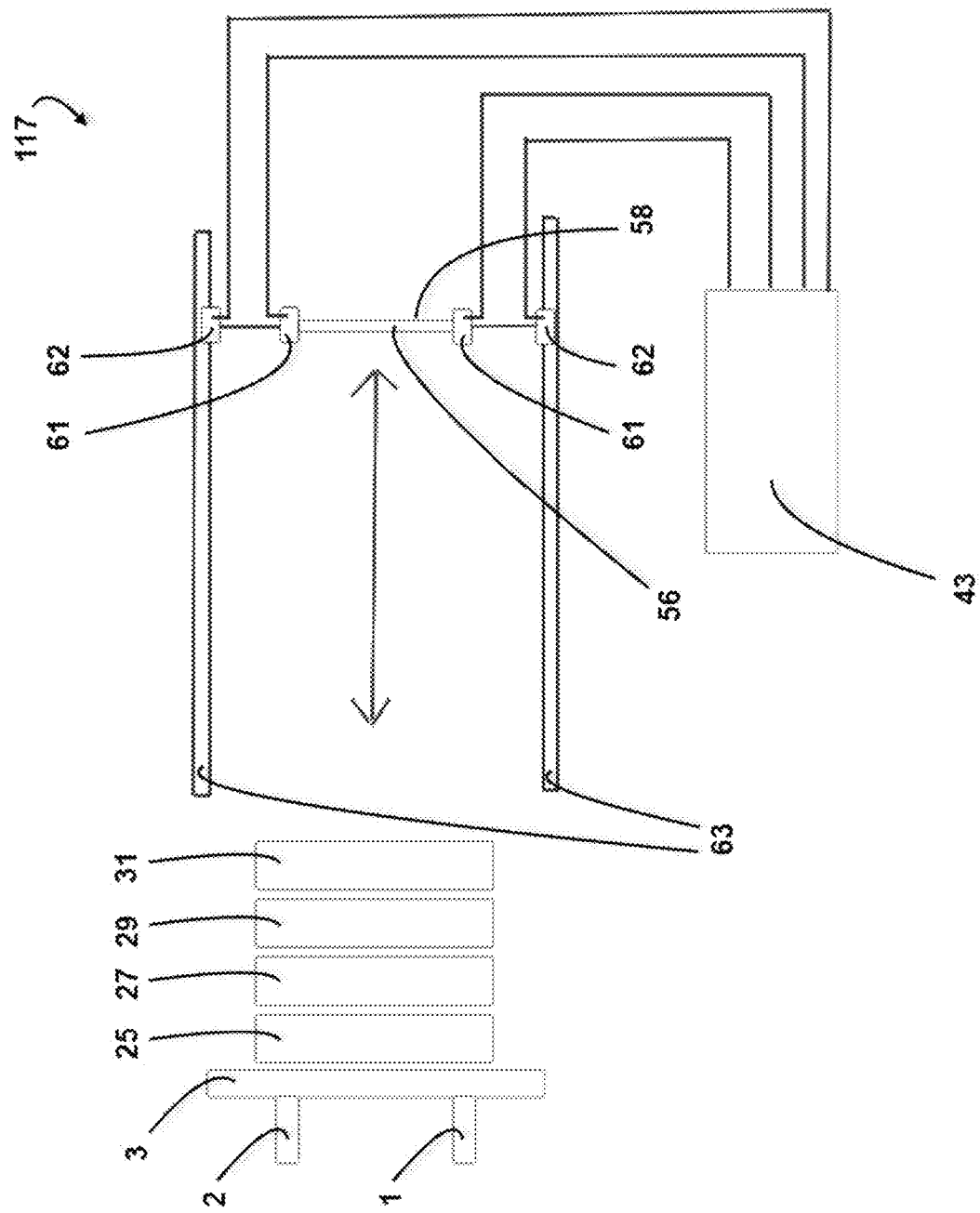
FIG. 8 illustrates a system for switching between near and far vision tests, as well as testing near vision at different distances in accordance with some embodiments of the invention.

FIG. 8 illustrates a system 117 for switching between near and far vision tests, as well as testing near vision at different distances. The system 117 may comprise one or more actuators for actuating a rotational movement of a rotating mirror for switching between near and far vision test. In an example, the system 117 may comprise motor gears 61, motorized ball screws 62 and ball screw guide rails 63. Motor gears 61 may be connected to and rotate a rotating mirror 56 in such a way that it reflects light rays towards the user from a distant vision test such as a mirror box 5. Motor gears 61 may also rotate the rotating mirror 56 in such a way that a posteriorly attached near vision test chart 58 is facing the user when refracting near vision. Near vision may further be refracted at different near distances via motorized ball screws 62 moving a near vision test chart 58 along ball screw guide rails 63.

It is important to understand that a system 117 may be used to place different eye tests at different distances in front of a user's eye(s). For example a digital acuity chart with test images configured for near and distant vision refraction may be moved along the path of the ball screw guide rails 63.

The actuators may be controlled to drive the rotational movement of the rotating mirror in response to a user command. An operating unit and processor 43 may be configured to generate instructions to the actuator when a user command is received. In some cases, the rotating mirror may be rotated manually or in a non-motorized fashion.

FIGS. 9A-C illustrate a system 117, placing a near vision test chart 58 positioned at multiples distances in accordance with some embodiments of the invention. In some embodiments, the near vision test chart 58 can be positioned at varied distance ranges corresponding to various situations where an eyewear may be used in everyday life. In some embodiments, a distance range may correspond to a common situation where an eyewear can be used. For instance, different distance ranges may correspond to reading glasses used for reading an object at different distances. FIG. 9A depicts a system 117 at a first close distance range for refracting a user's vision. When the near vision test chart 58 is positioned within the first close distance range, the near vision tests may be used for determining reading glasses used for tasks such as sewing, fly-tying, soldering, and the like. FIG. 9B depicts a system 117 at a second near distance range. When the near vision test chart 58 is positioned within the second near distance range, the near vision tests may be used for determining reading glasses used for refracting at book reading distance and the like. FIG. 9C depicts a system 117 at a third near distance range for refracting a user's vision. When the near vision test chart 58 is positioned within the third close distance range, the near vision tests may be used for determining reading glasses used for computer monitor reading distances, music reading distances, such as playing a piano and the like. Various ways may be used for segmenting the near distance ranges. The system 117 may be adjusted or preprogrammed to test at any number of other distances.

In some embodiments, each distance range may comprise a base distance where other distances within the range may be offset from the base distance. The increment within each distance range may or may not be the same. In some cases, a user may be allowed to choose a distance range first then perform the fine adjustment within the distance range. For example, a user may be asked to select from "computer reading glasses," "book reading glasses," "very near vision reading glasses," "stand near vision glasses" or "far vision glasses" and the like. This may provide an efficient and accurate vision test.

In some embodiments, vision test results may be provided according to the different distance ranges. In some embodiments, a user may be provided a reading glass number according to the corresponding distance range. In some cases, the reading glass number may be provided using different numbering methods when in different distance ranges. For example, to convert a number tested in the standard distance range into a number in the computer reading distance range, the software may half the standard near vision number and then round down to the nearest quarter diopter. For instance, if a user measures +2.0 for reading glasses, then for computer glasses, the result may be +1,0. If they were a +2.25, then for computer glasses the result may be +1.0 (half of +2.25 rounded down do the nearest quarter diopter). In another example, if a user measures +2.25 on the standard near vision, the number may be +3.25 for very near vision glasses.

FIGS. 10A-B illustrate a system 117 for testing near and far vision using a digital acuity chart 49 in accordance with some embodiments of the invention. The digital acuity chart may have a configurable operating distance of six feet or less, along with a posteriorly attached near vision test chart 58. The digital acuity chart 49 is rotatable via motor gears 61. FIG. 10A depicts a system 117 in a distance vision refraction configuration wherein a digital acuity chart 49 is facing the user. A near vision test light source 60 is turned off in this configuration. FIG. 10B depicts a system 117 in a near vision refraction configuration with a near vision test chart 58 facing the user. A near vision test light 60 is on in this configuration. In other embodiments a digital acuity chart 49 may be configured with images, which allow for refraction at different near distances and at optical infinity, thus making a near vision test chart 58 obsolete.

Figure 25A:
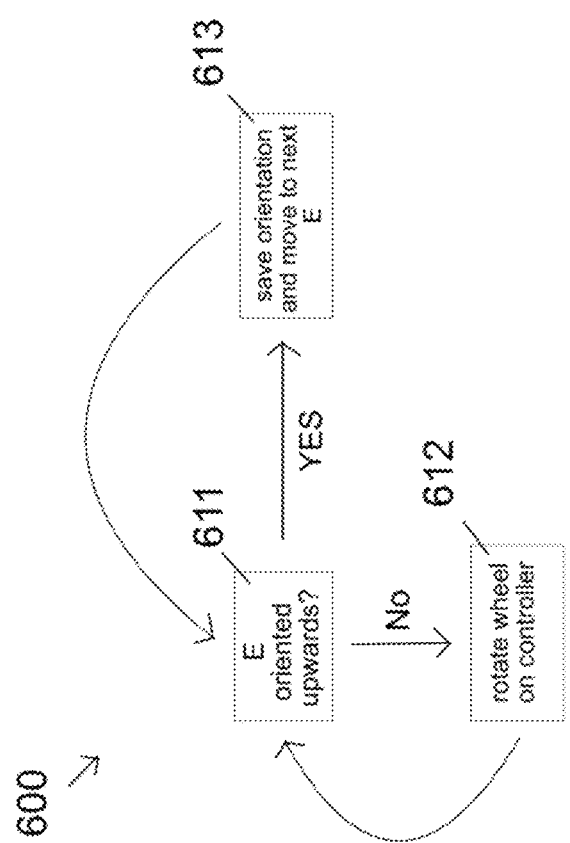
FIGS. 25A-C show an exemplary visual acuity verification system, in accordance with embodiments of the invention.
Figure 25B:
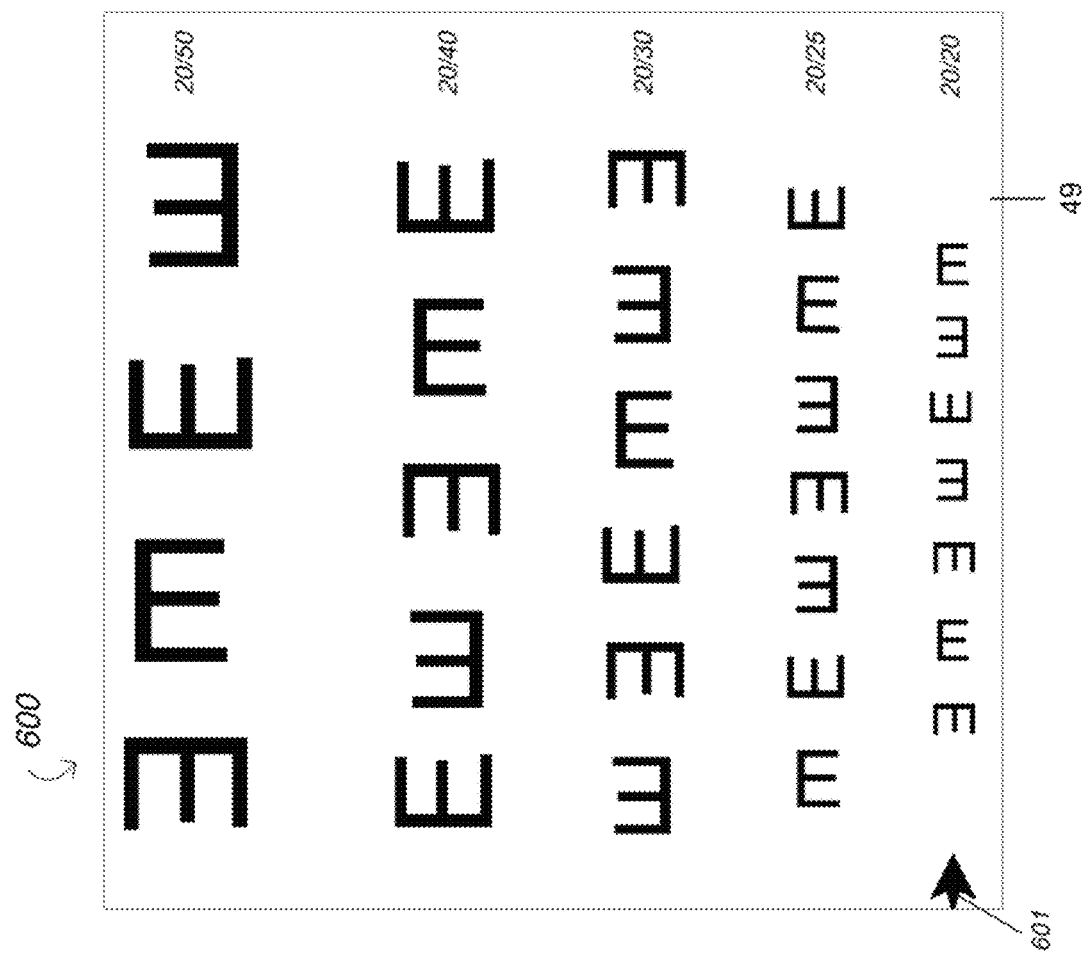
Figure 25C:
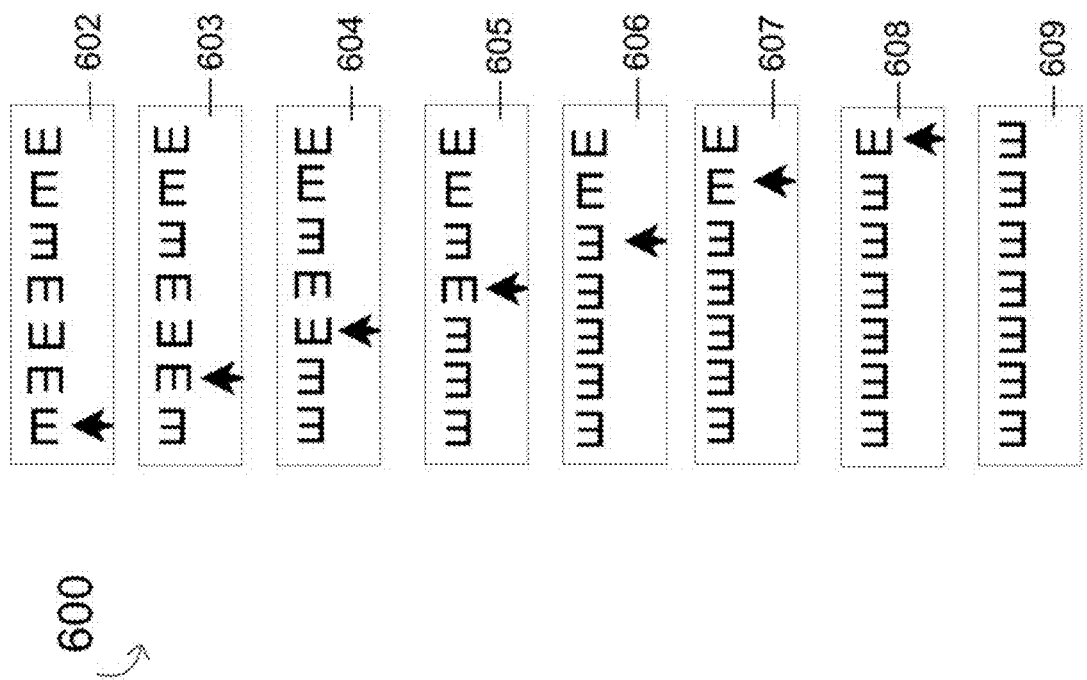

In some embodiments, the system 117 may comprise a visual acuity verification/assessment system for vision self-testing. FIGS. 25A-C show an exemplary visual acuity verification system 600 in accordance with embodiments of the invention. FIG. 25A shows a flow diagram of the steps and preprogramming involved in a visual acuity verification system 600. System 600's hardware may comprise a digital acuity chart 49, a control unit 10, and operating unit and processor 43. In preferred embodiments, system 600 would thus be incorporated into a system 117, so that visual acuity could be verified as in step 153 of automated SSR system 169. The preprogramming allows the user to verify their visual acuity by first finding the lowest line they can read on a tumbling E chart and then orienting upwards all of the E's for that line. The process starts by first asking the user if a particular E is oriented upwards 611.

If the user answers "no" then they are instructed to rotate the wheel on control unit 10 until the E is oriented upward 612. The axis control wheel 70 only rotates one E at a time on the digital acuity chart 49, which displays the tumbling E's. Clockwise rotation of the axis control wheel 70 causes clockwise rotation of the selected E, while counter clockwise rotation of the axis control wheel 70 causes the E to rotate in the opposite direction. The user is instructed to press the X button 67 once the E is oriented upward. Pressing the X button 67 takes the user back to stage 611 in the program, regardless if the E is correctly oriented upwards and the result for that E is saved.

If the user answers "yes" (i.e. the E was already oriented upwards according to the user's vision) then he/she is instructed to press the X button 67, which takes them back to stage 611.

When system 600 is incorporated into system 169, the axis control wheel 70 will not affect the axis of the cylindrical component during this stage of the preprogramming. Once the user has attempted to correctly orient all of the E's for that line, their verified visual acuity results are displayed.

The user may go back to reorient any of the previous E's at any time by pressing the left button 74 as needed. They may use the right button 72 to go forward.

FIG. 25B illustrates how the lowest line that can be read on a tumbling E chart (e.g. 20/20 line) may be selected by using a pointer 601 on a digital acuity chart 49 using system 600. The up button 71 and down button 73 on control unit 10 may be used to make the selection, before confirming the selection by pressing the X button 67.

FIB. 25C illustrates how the sequence of screenshots may look for someone with perfect 20/20 vision after using system 600. Screenshot 602 shows that the first E for that line has been selected. After the user orients the E in the direction that they believe to be upward and presses the X button 67, they are taken to the next E 603. This process continues 604, 605, 606, 607, 608, until the user finishes 609. For a user who selected the 20/20 line in FIG. 25B and then oriented every E correctly as in FIG. C, their verified visual acuity results may be displayed as "20/20 100%" meaning that they were able to correctly read each letter on the 20/20 line. To ensure understanding of the test, the user may be shown a quick tutorial with one very large E that is shown in the upward orientation so that the user know how to correctly perform the test.

Figure 11:
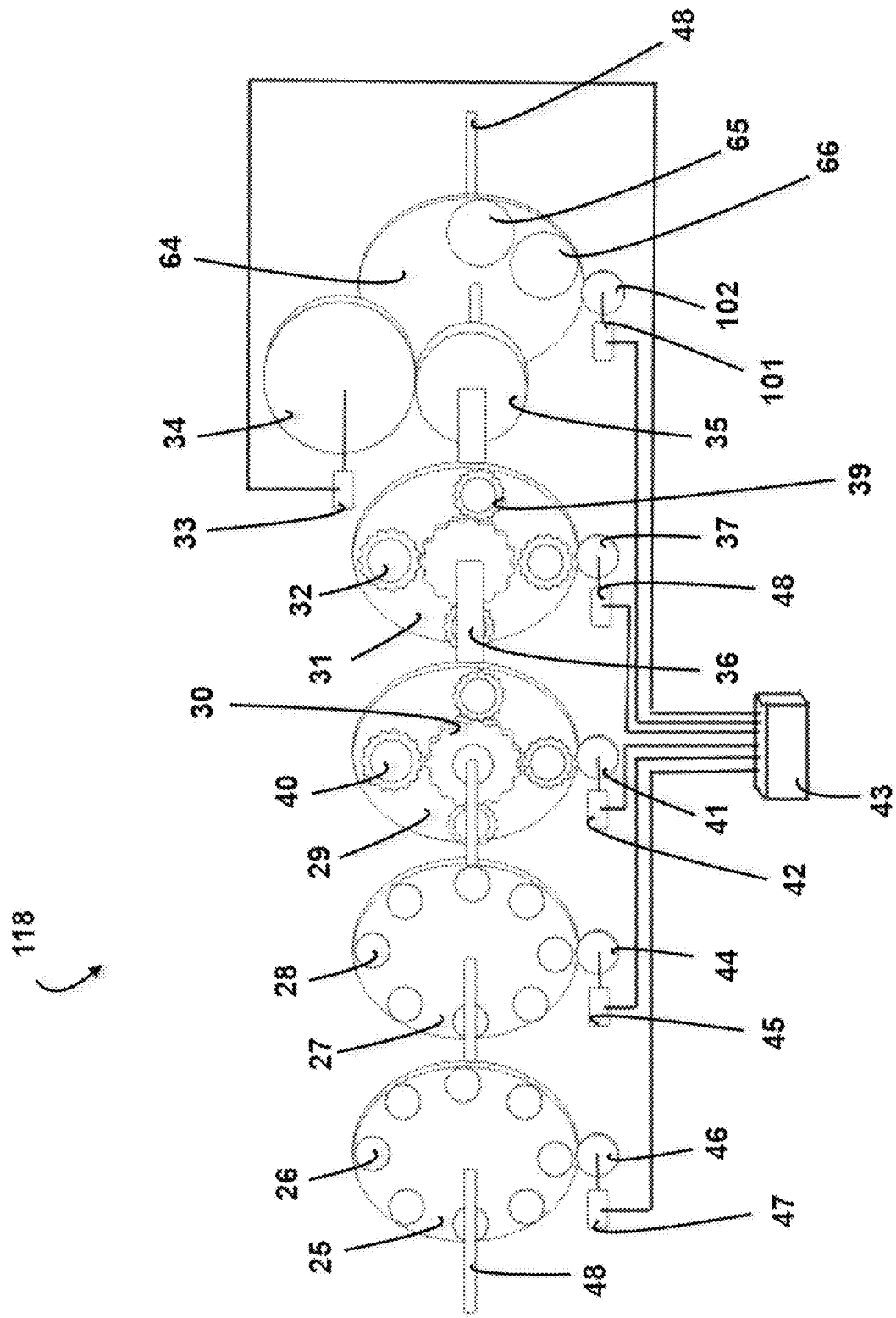
FIG. 11 is an expanded view of some components of a lens chamber with focus on a collimating lens used to create optical infinity within a smaller test space in accordance with some embodiments of the invention.

FIG. 11 illustrates a system 118 for creating parallel light rays for a vision test in accordance with some embodiments of the invention. A collimating lens 65 may be used for creating the parallel light such that distant vision refraction can be performed in a short distance rather than the standard 20 feet or 6 meters. A collimating lens is used to cause divergent light rays to become parallel. Thus, when looking at a near object through a collimating lens, the eye may perceive the near object as being much farther away than it actually is. System 118 may comprise a collimating lens 65 along with a plano lens 66, both of which may be placed on a rotating lens disk 64. A motor 101 and a pinion 102 may power rotation of a lens disk 64. Non-parallel light rays from a vision test placed much closer than the standard 20 feet may enter a collimating lens 65 and then exit with a parallel orientation. Thus, the eye perceives these light rays as emanating from an object placed at optical infinity. After exiting a collimating lens 65, the light rays enter at least one trial lens in the user's optical path. The user then refracts for distant vision using different trial lenses. A plano lens 66 may also be placed on a lens disk 64 for the purpose of allowing the user to switch between distant and near refraction. When switching to near vision refraction, a system 118 would rotate a collimating lens 65 out of a user's optical path and rotate a plano lens 66 into a user's optical path. The user then refracts for near vision using different trial lenses. The digital acuity chart used for distance refraction may remain in the same position or be placed closer to a lens disk 64 during near vision refraction.

Figure 12A:
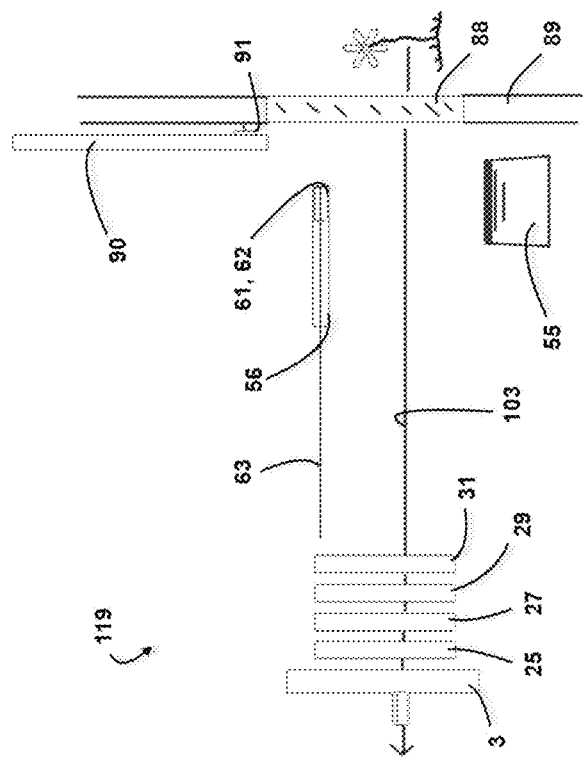
FIGS. 12A-B illustrate a system for switching between acuity vision testing and quality vision testing in accordance with some embodiments of the invention.
Figure 12B:
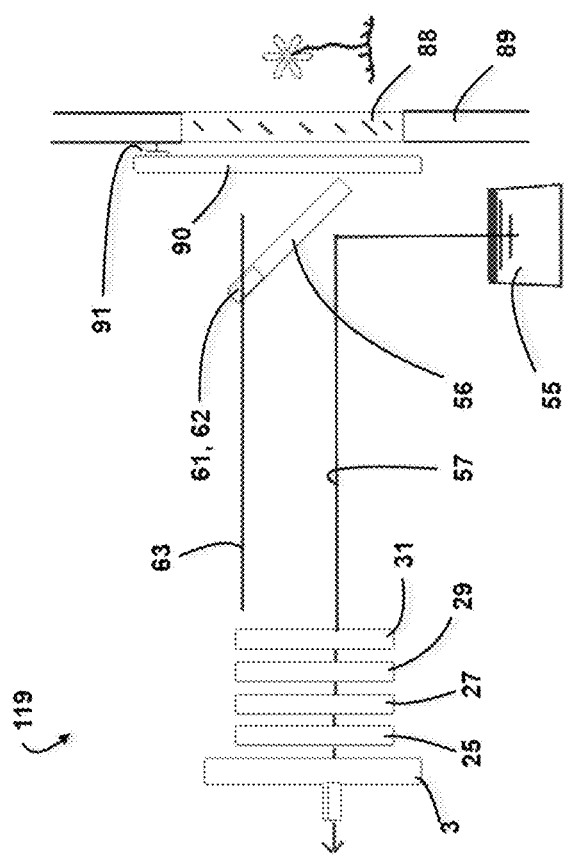

FIGS. 12A-B illustrate a system 119 for switching between acuity vision testing and quality vision testing in accordance with some embodiments of the invention. Quality vision testing may comprise having a user viewing real word objects for testing the quality of the lenses. System 119 may comprise a visual quality window 88, a window cover 90, and a window cover motor gear 91.

FIG. 12A shows a system 119 in a visual acuity configuration. A pivoting mirror 56 may be positioned in order to reflect optical infinity light rays 57 through at least one trial lens in a user's optical path. The optical infinity light rays 57 may emanate from a series of mirrors within a mirror box; the last mirrors in the series are represented herein by mirrors 55 and 56, respectively. A digital acuity chart, an illuminated eye chart and the like may be used in place of the mirror box. In this particular embodiment, a window cover 90 may be used to block outside light from entering the device. A collimating lens system 118 may be placed between a pivoting mirror 56 and trial lenses for the purpose of decreasing the space required for distance acuity refraction.

FIG. 12B shows a system 119 in a visual quality configuration. When refracting for visual quality, a pivoting mirror 56 and a window cover 90 may be rotated out of a user's optical path or a user's viewing direction by motor gears 61 and 91, respectively. This allows for visual quality light rays 103 emanating from objects outside of the device to enter the device along a user's optical path.

Various other systems or methods can be used to allow a user to switch between refracting for visual acuity and refracting for visual quality using the provided systems and methods.

FIG. 13A illustrates a refractor 7 wherein a visual quality window 88 has replaced a mirror box 5. In this particular embodiment of a refractor 7, visual quality alone may be tested, however other tests may be added outside a window 88. In some cases, the visual quality window 88 may be part of the wall of a lens chamber 4. For illustrative purposes, the wall of lens chamber 4 has been cross-sectioned and labeled.

FIG. 13B and FIG. 13C both illustrate a refractor 7 which may use a system 119 for switching between refraction for visual quality and visual acuity. The refractor 7 may be the same refractor as described FIG. 13A with the addition of a system 119. The system 119 may comprise a pivoting digital acuity monitor 49, a visual quality window 88, and a window cover 99.

FIG. 13B shows a system 119 in the visual quality configuration, wherein a window cover 90 and a digital acuity chart 49 are positioned out of a user's optical path. The window cover and the digital acuity chart may be rotated by the motor gears 61 and 91 respectively.

FIG. 13C illustrates a system 119 in the visual acuity configuration, wherein a window cover 90 blocks any outside light from entering a lens chamber 4 and a digital acuity chart 49 is positioned in a user's optical path. Digital acuity chart 49 and window cover 90 are powered into position again via motor gears 61 and 91, respectively. In this configuration, a digital acuity chart 49 may be configured with test images for distant and near vision acuity testing. A digital acuity chart 49 may slide closer to the user's eye for near vision refraction via motorized ball screws 62 riding along ball screw guide rails 63. During distant acuity refraction and near vision acuity refraction, optical infinity light rays 57 and near vision test light rays 100, may travel along a user's optical depending on how far a digital acuity chart 49 is positioned from a user's eye.

In other embodiments, a digital acuity monitor 49 may act as a window cover, when switching between visual acuity refraction and visual quality refraction. This may occur by way of a sliding mechanism that keeps a digital acuity monitor 49 tightly fitted against the wall of a refractor 7 as it is positioned over a window 88. This may correspond to the configuration for visual acuity refraction. A digital acuity monitor 49 may be positioned out of the user's optical path exposing a user's eye to a window 88 for visual quality refraction.

FIG. 14 illustrates a table illustrating a plurality of optical elements and their position on each lens disk in accordance with some embodiments of the invention.

Figure 15:
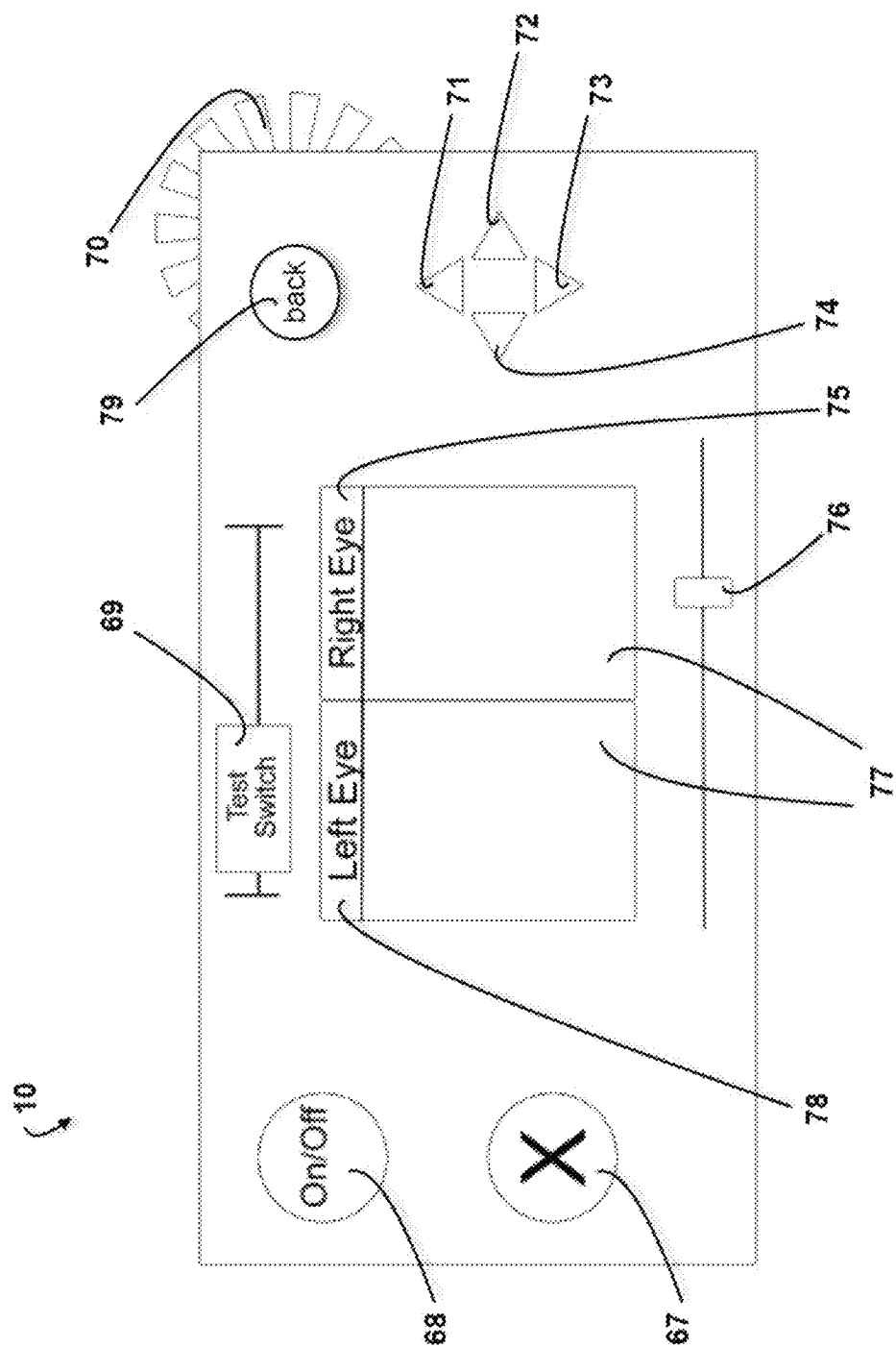
FIG. 15 illustrates the many functions of a control unit in accordance with some embodiments of the invention.

FIG. 15 illustrates a hand-held control unit 10 which a user may interact with during SSR in accordance with some embodiments of the invention. A control unit 10 may comprise an on-off button 68 that turns the invention on or off. In other embodiments, the invention may automatically turn off if left unused for a pre-determined amount of time or turn on using voice command technology. A control unit 10 may comprise an input device such as a test switch 69 that allows a user to select which eye is being tested. In some embodiments, a control unit 10 may comprise an up button 71, which may cause negative 0.25 diopter (D) changes to either the spherical or cylindrical components; and a down button 73, which may cause positive 0.25 D changes to either the spherical or cylindrical components. Various other input devices may be used for a user to input the diopter. For example, a dial may be turned left/right to increase to decrease the diopter. The dial may be snapped in to discrete positions that corresponding to a step in adjusting the diopter. The step or increment for adjusting the diopter may or may not be the same when in different distance ranges. Larger or smaller diopter steps may be used for adjusting the spherical or cylindrical components.

An X button 67 may be used to toggle an up button 71 and a down button 73 between controlling for only changes in the spherical component and controlling for only changes in the cylindrical component. An X button 67 may also be used along with pre-programming, to guide a user through the SSR process. A left button 74 and a right button 72 may be used to provide verification of a user's visual acuity during the SSR process. These buttons may also be used to measure a user's PD. A volume adjuster 76 allows a user to adjust the volume of auditory instructions, which may be transmitted via headphones 9. A back button 79 may allow a user to go back one step in the SSR process.

Figure 16:
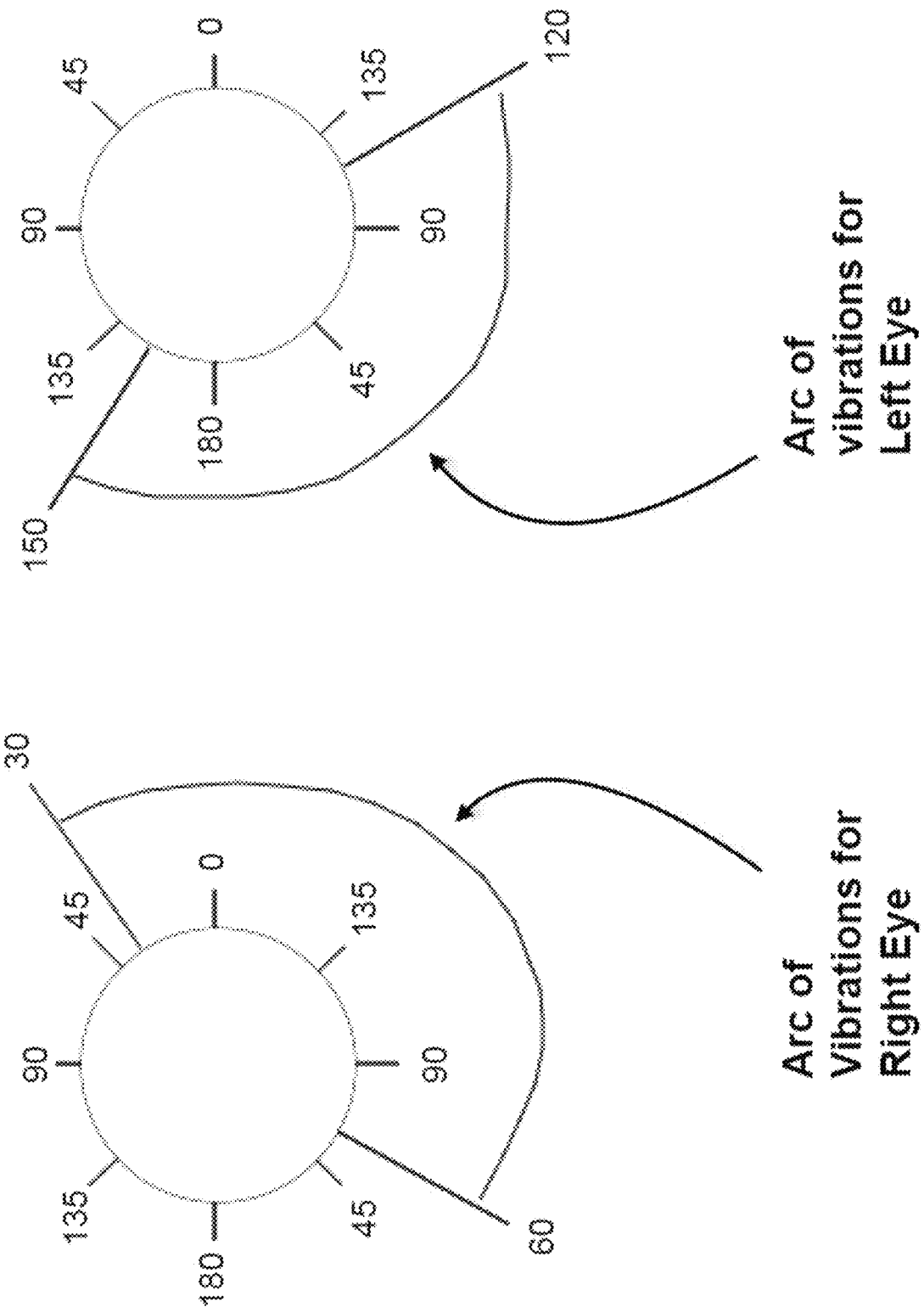
FIG. 16 illustrates the degrees in which a control unit will vibrate when using a control unit to find the cylindrical axis in accordance with some embodiments of the invention.

Cylindrical axis control wheel 70 may be used to make continuous fine-tuned adjustments to the axis of the cylindrical component. A wheel 70 may rotate the axis of the cylindrical component clockwise or counter clockwise, depending on which direction a wheel 70 is rotated. A control unit 10 may vibrate if the user rotates the wheel outside an approximate 180-degree arc which signals a user to rotate the axis control wheel 70 in the opposite direction. This is further illustrated by FIG. 16. The purpose of these vibratory signals is to speed up the process of diagnosis and refracting for astigmatism during the SSR process.

A display screen 77 may be used to display information to a user, such as refractive measurements, PD, VD, and the like. A right eye label 75 and a left eye label 78 may be used to orient a user as to which eye they are currently testing, which depends on the position of test switch 69. Label 75 and 78 may be further used to ensure refractive measurement and other data is recorded for the correct eye.

FIG. 17 further illustrates some of the data, which may be displayed on a display screen 77 for each eye. This may comprise refractive measurements, verified acuity data, VD, PD, and the like. A display screen 77 may also comprise other display items such as advertisements, contact information, or other instructional material.

FIG. 18A-C illustrates three different automated systems for measuring the refractor VD. Each system measures the VD from the user's end of an eyepiece 1 or 84, to a series of trial lenses 80.

FIG. 18A illustrates a system 120 comprising voice commands and an eyepiece 1. An eyepiece 1 may have a predetermined length. This predetermined length is used to standardize the VD for each user. During the SSR process, a user is asked to keep their eye snug against an eyepiece 1. Since a user's end of an eyepiece 1 is stationed at a fixed and predetermine length from the trial lenses, a standardized VD for each user can be achieved.

FIG. 18B and FIG. 18C allow for further accuracy when measuring the VD.

FIG. 18B illustrates a system 121 comprising an eyepiece, of which the wall is cross-sectioned and labeled 84 for illustrative purposes. Further comprising a system 121 is a laser emitter 81, lasers beams 82, and a laser detector 83. During SSR, laser beams 82 are intercepted by a user's corneal surface 87. Laser beams 82, which are not intercepted, will become detected by a laser detector 83. The transition point at which lasers start becoming intercepted by corneal surface 87 is used to measure the distance to the trial lenses or the VD.

FIG. 18C illustrates a system 122 comprising a camera 85 and a ruler 86 printed on the inner surface of an eyepiece. A camera 85 may line up a user's corneal surface 87 to a point on a ruler 86. An operating unit and processor 43 may determine the VD so it may be presented on display screen 77.

FIGS. 19A-C illustrates a system 123 in accordance with some embodiments of the invention. The system 123 may comprise a mirror 94, a headrest 95, a motorized ball screw 96, a ball screw guide rail 97, a PD needle 98 and a headrest mount 99.

FIG. 19A illustrates a front view of a system 123, which may be mounted to a front cover 3. A user is instructed to place their forehead against a headrest 95 and close one eye while looking straight into mirror 94 with their other eye. Control unit 10 may be used to move a PD needle 98, so that it is in line with the center of a user's pupil. The provided systems may record the position of the user's first pupil. Next, a user closes their open eye and opens their other eye. A user lines up PD needle 98 with their other pupil. Based on these measurements, the provided system calculates the distance from the previous to the current position of the PD needle 98. This represents the PD, which may be displayed on a display screen 77. In other embodiments with two lens chambers that allow for simultaneous refraction of both eyes, PD distance may be calculated by sliding the lens chambers along a rail, through manual or automated means.

FIG. 19B illustrates a side view of system 123. Headrest mount 99 fastens and stabilizes a headrest 95 to a front cover. For illustrative purposes, the front cover has been cross-sectioned and labeled 93. A ball screw guide rail 97 can be seen mounted to a headrest 95 in this side view. A PD needle 98 can be seen lined up with a right eye 22.

FIG. 19C illustrates a system 123 from a bird's eye view. A motorized ball screw 96 with its attached PD needle 98 (not seen from this view) rides left and right on a ball screw guide rail 97. This is a different view of the same configuration as seen in FIG. 19B. In this view, the same right eye 22 is lined up with a motorized ball screw 96.

Figure 20:
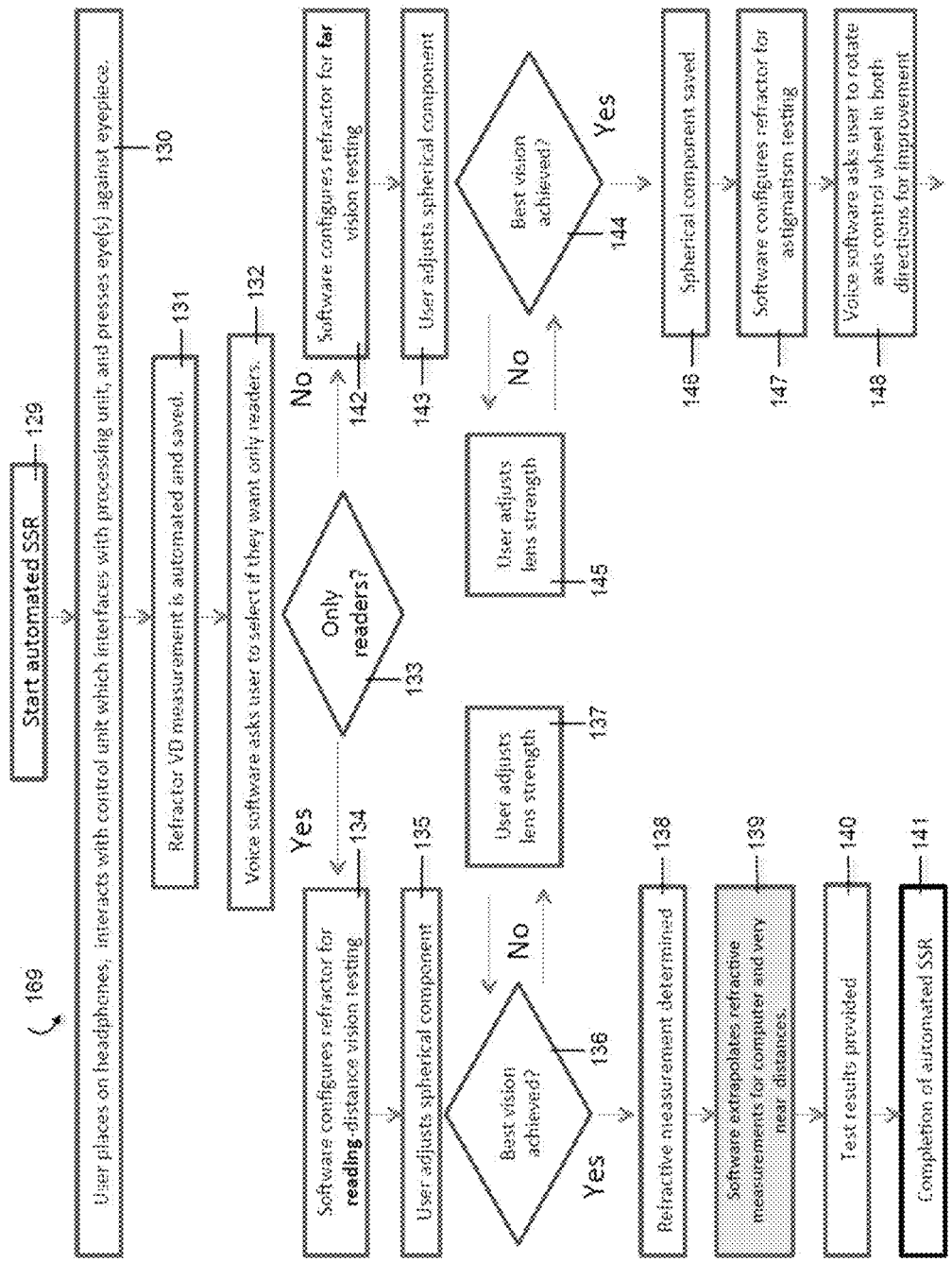
FIG. 20 and FIG. 21 show an example of an automated subjective self-refracting (SSR) process using a SSR system in accordance with some embodiments of the invention, in accordance with some embodiments of the invention.
Figure 21:
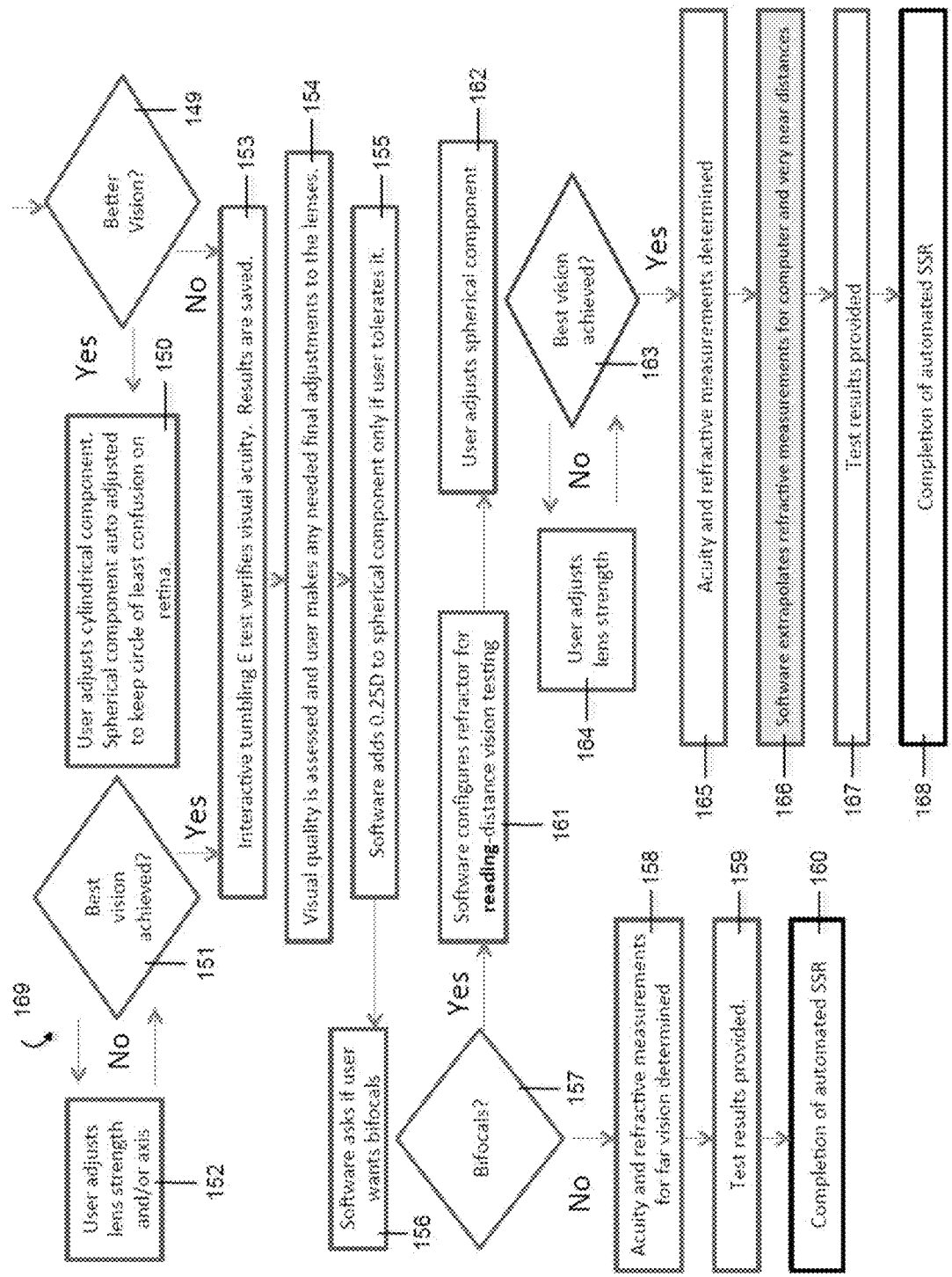

FIG. 20 and FIG. 21 show an example of an automated subjective self-refracting (SSR) process using a SSR system 169 in accordance with some embodiments of the invention. The SSR system 169 may comprise a refractor device as described elsewhere herein. The SSR system 169 can be implemented by software, hardware or a combination of both. The automated SSR process may be initiated 129 with a voice command, a user's interaction with a control unit 10, motion detection of a user, and the like. The automated SSR system 169 then sets the user up for SSR 130 by instructing them to apply a set of headphones 9, followed by a quick tutorial on the use of a control unit 10, and finally by having the user apply their eye(s) to eyepiece(s) 1 or 2. Next, system 169 automates and saves the refractor VD 131. The user is then asked by preprogrammed voice commands whether they want only reading glasses only 132. The user may provide input 133. System 169 receives the answer from the user via voice recognition software or control unit input, 10 or the like.

If the user answers "yes," then a refractor 7 is configured for reading-distance vision testing 134. In some embodiments, a user may be further provided options to choose from different distance ranges or reading distances. For example, a user may be asked to choose form "computer reading glasses," "book reading glasses," "very near vision reading glasses," "stand near vision glasses" and the like.

Upon selection of a category, the user may be guided by a series of preprogrammed voice commands, beginning with adjustment of the spherical component 135, followed by subjective self-assessment of visual acuity and/or quality 136. Voice commands instruct the user to keep adjusting the spherical power 137 until best vision is achieved 136. Once best vision is achieved, the exact refractive measurements are determined 138. Special software programming then calculates the appropriate refractive measurements for computer monitor reading distance and very close up working distance 139. The three refractive measurements (i.e. for reading at computer monitor distance, book distance, and very close working distance) are displayed to the user, stored on FOB 8 or transmitted to the user using email, text messaging, web-application or the like 140. The system completes the automated SSR process 141. Completion of the automated SSR process 141 may include but is not limited to allowing the user to receive a prescription, order eye wear, procure eye wear at the location, book an office appointment with an eye care professional or interact with an eye care professional in real time with an audio-video feed.

If the user answers "no" then a refractor 7 is configured for far distance vision testing 142. The user follows a series of preprogrammed voice commands, beginning with adjustment of the spherical component 143, followed by subjective self-assessment of visual acuity and/or quality 144. Voice commands instruct the user to keep adjusting the strength of the spherical component 145 until best vision is achieved 144. Once best vision is achieved, system 169 saves the spherical component refractive measurements 146.

Next, system 169 is configured so that a refractor 7 can test for astigmatism 147. Voice software asks the patient to rotate axis control wheel 70 in both directions 148 and if there is any improvement in vision, to stop on the axis with the clearest vision. Next, the preprogrammed voice instructions ask the user whether or not their vision was improved 149. If the user answers "yes" they are asked to adjust the cylindrical power to check for more visual improvement 150. System 169 now auto-adjusts the spherical component to keep the circle of least confusion on the retina, while changes are made to the cylindrical component. The user is then asked if best vision is achieved 151 and if not, the user continues to adjust the cylindrical lens power and/or axis 152 until best vision is achieved 151. Once best vision is achieved, the user is taken to a novel interactive visual acuity assessment test 153. The user is also taken to the same visual acuity test 153 if they answered "no" to question 149, which excludes the diagnosis of astigmatism.

The visual acuity assessment test 153 is conducted by having the user select the lowest line he/she can read on a digital tumbling E chart. The tests may rely on a user turning an axis control wheel 70 which rotates each of the E's so they all point upwards. When finished, system 169 saves the lowest line that was selected (e.g. the 20/20 line) and the percentage of E's in that line that were correctly oriented to point upwards (e.g. 100%). In this way, the system 169 measures the user's visual acuity and also verifies the result (i.e. as a percentage of the number of correctly oriented E's) without the need for assistance from another person. Next, visual quality is assessed and the user is instructed to make any needed final adjustments 154.

System 169 then adds positive 0.25 D to the spherical component only if it improves or causes no change in the visual acuity 155. This is to help keep the ciliary muscles in the eye relaxed when looking at near objects.

The user is then asked if they would like bifocals 156. User chooses either "yes" or "no" 157. If the user answers "no" the acuity and refractive measurements for far vision are determined 158. This data is displayed to the user, stored on FOB 8 or transmitted to the user using email, text messaging and the like 159. The system completes the automated SSR process 160. Completion of the automated SSR process 160 may include but is not limited to allowing the user to receive a prescription, order eye wear, procure eye wear at the location, book an office appointment with an eye care professional or interact with an eye care professional in real time with an audio-video feed. If the user answers "yes," then a refractor 7 is configured for near vision testing 161. The user follows a series of preprogrammed voice commands, beginning with adjustment of the spherical component 162, followed by subjective self-assessment of visual acuity and/or quality 163. Voice commands instruct the user to keep adjusting the strength of the spherical component 164 until best vision is achieved 163. Once best vision is achieved, the far vision acuity along with the far and reading distance vision refractive measurements are determined 165. System 169 extrapolates the refractive measurements for both computer distance work and very near vision work (e.g. fly tying) from the data previously gathered at near distance 166. This data is displayed to the user, stored on FOB 8 or transmitted to the user using email, text messaging and the like 167. The system then completes the automated SSR process 168. Completion of the automated SSR process 168 may include but is not limited to allowing the user to receive a prescription, order eye wear, procure eye wear at the location, book an office appointment with an eye care professional or interact with an eye care professional in real time with an audio-video feed. Table 1 lists written instruction, a series of voice commands, along with preprogramming, and an algorithmic process in accordance with the preferred embodiment of the SSR process as illustrated in FIG. 20. The algorithmic process (i.e. 301-330), along with software and preprogramming of an operating unit and processor 43, together may employ a system 110, in order to take a user through the SSR process.

TABLE 1

| | |
|---|---|
| 200 | Written Instruction<br>Place the headphones over your ears and press the On/Off button. Adjust the volume on the controller as needed. Follow the voice commands to test your vision. |
| 301 | Stage 1 of Program Algorithm:<br>After the user presses the On/Off Button 68 on Control Unit 10, the user is taken to Voice Command Number 1. |
| 201 | Voice Command Number 1:<br>Welcome to Vipassana, your partner in seeing things as they truly are. Now place the controller in your hands. Practice pressing the up and down buttons with your thumb. You will use these buttons to change the power of the lenses. Next, place your finger on the wheel of the controller and practice rotating it in both |

TABLE 1-continued

| | |
|---|---|
| | directions. You will use this wheel to change the axis of the lenses. Next, press the X button. You will use this button to change the type of lenses. Now lets get started. Slide the test switch on the controller to the other side. |
| 302 | Stage 2 of Program Algorithm:<br>Sliding the Test Switch 69 to the other side after Voice Command Number 1 causes all 4 Disks 25, 27, 29, 31 to rotate in such a way that the center of each Plano lens FIG. 14 is centered on optical path 23 or 24 for the eye selected 21 or 22 depending on which eye label 75 or 78 the Test Switch 69 is resting over on Control Unit 10. |
| 202 | Voice Command Number 2:<br>If you are only interest in reading glasses without correcting for astigmatism press the X button. If not press the up button. |
| 303 | Stage 3 of Program Algorithm:<br>Pressing the X Button 67 after Voice Command Number 2 sets the system up for the Add 2 Near Vision Test FIG. 9B (other embodiments may suffice for this stage of near vision testing as depicted in FIG. 13C). The appropriate eyepiece light 17 or 18 will flash for a few seconds. The user is then taken to Voice Command Number 20.<br>If Up Button 71 is pressed after Voice Command Number 2, each Plano lens will remain centered on the user's optical path 23 or 24 and the appropriate eyepiece light 17 or 18 will flash for a few seconds. The user is taken to Voice Command Number 3. |
| 203 | Voice Command Number 3:<br>Look into the eyehole that is flashing. |
| 304 | Stage 4 of Program Algorithm:<br>After Voice Command Number 3 the user is taken to Voice Command Number 5. |
| 204 | Voice Command Number 4:<br>Now look into the other eyehole that is flashing. |
| 305 | Stage 5 of Program Algorithm:<br>After Voice Command Number 4 the user is taken to Voice Command Number 5. |
| 205 | Voice Command Number 5:<br>Make sure your eye is snug against the eyepiece. Close your other eye. Now focus on the lowest line that you can see. Try not to tilt your head left or right. Now start pressing the up button to see if it improves your vision.<br>You may press the down button to go in the other direction. Keep making adjustments until you can clearly see the direction each E is pointing on the lowest line that you can. Take your time.<br>After you find the lowest line you can read, press the X button. |
| 306 | Stage 6 of Program Algorithm:<br>During Voice Command Number 5, the Up and Down Buttons 71 and 73 will only cause −/+0.25D changes respectively in the Spherical Component.<br>Pressing the X Button 67 after Voice Command Number 5 causes optical element 4 on disk L-CYL FIG. 14 to be moved into optical path 23 or 24 depending on which eye the Test Switch 69 has selected. Pressing X Button 67 after Voice Command Number 5, also manipulates H-SPH Disk 25 and L-SPH Disk 27 in such a way that (+) 0.25D is added to the Spherical Component. This keeps the circle of least confusion on the retina, while testing for astigmatism. The axis of optical element 4 on disk L-CYL FIG. 14 at this stage will start at 60 degrees during right eye refraction and 150 degrees during left eye refraction, according to FIG. 16. Control Unit 10 will vibrate in order to assist the user in keeping the axis within a predetermined 210-degree arc in order to speed up the refraction process FIG. 16.<br>Keeping the eye snug against the eyepiece will allow for standardization of the VD or auto-measurement depending on the embodiment used.<br>The user is taken to Voice Command Number 6. |
| 206 | Voice Command Number 6:<br>Now use your finger to rotate the wheel on the controller. Stop where the lowest line of E's that you can see is most sharp. The controller will vibrate when you have gone too far in one direction, so you will need to start turning the wheel in the other direction. Stop at a place along the wheel where the image is the sharpest and you can read the lowest line that you can. If the image does not get sharper anywhere along the wheel, then push the X button.<br>If you can find a place on the wheel where the image is slightly sharper, then press the up button. |
| 307 | Stage 7 of Program Algorithm:<br>Pressing the X button 67 after Voice command Number 6 causes the Plano lens FIG. 14 on H-CYL Disk 29 and L-CYL Disk 31 to line up on optical path 23 or 24, depending on the eye selected on control unit 10. H-SPH Disk 25 and/or L-SPH Disk 27 are manipulated in a way that removes the + 0.25D from the Spherical Component that was added in Stage 6 of Program Algorithm. The user is then taken to Voice Command Number 8.<br>Pressing the Up Button 71 after Voice Command Number 6, changes the Cylindrical Component by (−) 0.25D, the axis remains unchanged and the user is taken to Voice Command Number 7. |
| 207 | Voice Command Number 7:<br>Keep pressing the up button to see if the image gets sharper. You can press the down button to go in the other direction. Keep pressing either the up or down button until you find where the E's are the sharpest on the lowest line you can read. |

TABLE 1-continued

| | |
|---|---|
| | After finding the sharpest image with the up/down buttons, rotate the wheel again with your finger in either direction to see if you can make the E's on the lowest line you can read even sharper. When finished press the X button. |
| 308 | Stage 8 of Program Algorithm:<br>During Voice Command Number 7 the Up/Down Buttons 71 and 73 cause −/+0.25D incremental changes respectively in the cylindrical component.<br>The cylindrical lenses are manipulated in such a way that the axis of the Cylindrical Component is unchanged after each press of either the Up or Down Buttons 71 or 73.<br>The cylindrical lenses are also manipulated in such a way that the axis of the Cylindrical Component can be changed with Axis Control Wheel 70 between each press of either the Up or Down Buttons 71 or 73.<br>Also, during Voice Command Number 7, each −/+0.50D change in the Cylindrical Component results in same-time automatic changes of the Spherical Component that is half the magnitude and opposite the sign of the −/+0.50D change in the Cylindrical Component. Only −/+0.25D spherical changes are allowable, thus a −/+0.50D cylindrical change is needed. This is processed by Operating Unit 43 according to the following equation:<br>Corrective Spherical Change = (−½) Cylindrical Change in 0.50D increments<br>This is intended to keep the circle of least confusion on the retina, while the user is checking for astigmatism.<br>Pressing the X Button 67 after Voice Command Number 7 takes the user to Voice Command Number 8. |
| 208 | Voice Command Number 8:<br>Now use the Up and Down buttons to select the lowest line in which you can still see the direction that all the E's are pointing and then press the X button. |
| 309 | Stage 9 of Program Algorithm:<br>Each press of the Up or Down button 71 or 73 during Voice Command Number 8 will cause a different line to be highlighted and pressing X Button 67 will select the highlighted line on Digital Acuity Chart 49. A second line with the same number and size of E's will line up and appear under the line that was selected. Each E in this second line will have a different orientation than the E directly above it. The other lines on Digital Acuity Chart 49 will disappear. The user is then taken to Voice Command Number 9. |
| 209 | Voice Command Number 9:<br>A second row of E's of the same size, are now below the line you selected. Rotate the wheel with your finger to change the orientation of the E's in the second row so that they match the orientation of the E's in the first row. After orienting each E correctly use the Right to go to the next E. You may use the Left button to go back. Press the X button when finished. |
| 310 | Stage 10 of Program Algorithm:<br>During Voice Command Number 9 each E in the second line will be highlighted one at a time starting with the most left E. The user's visual acuity will be verified by orienting the E's in the second row using Axis Control Wheel 70. Pressing X Button 67 saves the visual Acuity for that line under the appropriate eye label FIG. 17, along with a percentage indicating the number of correctly oriented E's for that line.<br>The apparatus is then set up for assessing visual quality (e.g. FIG. 12B or FIG. 13B) depending on the embodiment chosen.<br>The user is then taken to Voice Command Number 10. |
| 210 | Voice Command Number 10<br>Now look out the window at objects that are 20 feet or further away. Use the up and down buttons if any further adjustment is needed improve the quality of your vision. You may use the Left and Right buttons to rotate the device and look left or right. Press the X button when finished. |
| 311 | Stage 11 of Program Algorithm:<br>The Up and Down Buttons 71, 73 cause −/+0.25D changes to the spherical component respectively during Voice Command Number 10. The Left and Right Buttons 74, 72 cause the apparatus to turn left and right respectively on a motorized swivel or other mechanism.<br>Pressing the X Button 67 at the end of Voice Command Number 10 takes the user to Voice Command Number 11, unless they were found to not have astigmatism during Voice Command Number 6, in which case they are taken to Voice Command Number 12. |
| 211 | Voice Command Number 11<br>Now turn the wheel on the controller with your finger if needed to improve the visual quality. When satisfied use the up and down buttons to make any further needed adjustments to your visual quality. When satisfied press the X button. |
| 312 | Stage 12 of Program Algorithm:<br>Pressing the X Button 67 at the end of Voice Command Number 11 saves the cylindrical component and axis to Display Screen 77, FIG. 17.<br>The user is then taken to Voice Command Number 12 |
| 212 | Voice Command Number 12:<br>You will now use the up and down buttons to go back and forth between two lenses.<br>Press the X button after finding the lens with the better quality of vision.<br>If you cannot find any difference between the two lenses, press the DOWN button one last time and then press the X button. |

TABLE 1-continued

313 Stage 13 of Program Algorithm:
The starting Spherical Component at the start of Voice Command Number 12 is called "Y." During this stage the user will see if his/her refractive error will benefit from adding + 0.25D to Spherical Component "Y." This new Spherical Component will be called "Y + 0.25." The Up and Down Buttons 71 and 73 will now only allow for changes between Spherical Components "Y" and "Y + 0.25." For example, if Up Button 71 is pressed and "Y" is in the user's optical path 23 or 24, then no further negative changes will be made to the Spherical Component. If the user then presses Down Button 73, the Spherical Component will be changed to "Y + 0.25" and further presses of the Down Button 73 will not cause any further positive diopter changes in the Spherical Component. This ensures that the final refractive measurement keeps the user's ciliary muscles relaxed as much as possible during accommodation.
Pressing the X Button 67 after Voice Command Number 12 saves the Spherical component for the far vision under the appropriate eye label on Display Screen 77, FIG. 17.
The user is then taken to Voice Command Number 13.

213 Voice Command Number 13:
If you do not want bifocals, progressive lenses, or reading glasses move the test switch to the other side.
If you want bifocals, progressive lenses, or reading glasses press the down button.

314 Stage 14 of Program Algorithm:
Moving the Test Switch 69 to the other side after Voice Command Number 13 takes the user to Voice Command Number 4, unless this was the second eye tested, in which case the user is taken to Voice Command Number 19. If taken to Voice Command Number 4 the appropriate eyepiece light 17 or 18 will flash for a few seconds.
Pressing the Down Button 73 at the end of Voice Command Number 13 adds (+) 0.25D to the Spherical Component and sets the system up for the Add 2 Near Vision Test FIG. 9B (other embodiments may suffice for this stage of near vision testing as depicted in FIG. 13C for example). The user is then taken to Voice Command Number 14.

214 Voice Command Number 14:
Keep pressing the down button until you can read the print clearly. Keep making adjustments with the down and up buttons as needed until the print is as clear as possible. When satisfied with your near vision, press the X button.

315 Stage 15 of Program Algorithm:
The Up and Down Buttons 71 and 73 make −/+0.25D changes respectively to the spherical component during Voice Command Number 14.
Pressing the X Button 67 after Voice Command Number 14 saves refractive measurements for Add 2 under the appropriate eye label on Display Screen 77, FIG. 17.
The user is then taken to Voice Command Number 15.

215 Voice Command Number 15:
If you would like glasses for reading at computer monitor distance press the up button. If you do not want glasses for computer monitor distance press the X button.

316 Stage 16 of Program Algorithm:
Pressing the Up Button 71 at the end of Voice Command Number 15 changes the Spherical Component by (−) 0.25D and sets the system up for the Add 3 Near Vision Test FIG. 9C (other embodiments may suffice for this stage of near vision testing as depicted in FIG. 13C for example). The user is then taken to Voice Command Number 17.
Pressing X Button 67 at the end of Voice Command Number 15 takes the user to Voice Command Number 16.

216 Voice Command Number 16:
If you would like glasses for very close work such as fly tying, sewing, or soldering press the down button. If you do not want glasses for very close working vision move the test switch to the other side.

317 Stage 17 of Program Algorithm:
Moving Test Switch 69 to the other side at the end Voice Command Number 16 takes the user to Voice Command Number 4. Unless this is the second eye test, in which case the user is taken to Voice Command Number 19.
Pressing the Down button 73 at the end of Voice Command Number 16 adds (+) 0.25D to the Spherical Component and takes the user to
Voice Command Number 19.

217 Voice Command Number 17:
Keep pressing the up button and down button as needed until you can read the print most clearly. When finished press the X button.

318 Stage 18 of Program Algorithm:
Pressing the X Button 67 at the end of Voice Command Number 17 saves refractive measurements for Add 3 under the appropriate eye label on Display Screen 77, FIG. 17.
The user is then taken to Voice Command Number 16.

218 Voice Command Number 18:
Keep pressing the down button and up button as needed until you can read the print most clearly. When finished move the test switch to the other side.

319 Stage 19 of Program Algorithm:
Moving Test Switch 69 to the other side at the end of Voice Command Number 18 saves refractive measurements for Add 1 under the appropriate eye label on TABLE 1-continued

| | |
|---|---|
| | Display Screen 77, FIG. 17.<br>The user is then taken to Voice Command Number 4.<br>If this was the second eye tested, then the user is taken to Voice Command Number 19. |
| 219 | Voice Command Number 19:<br>If you would also like to measure your pupillary distance for better fitting of eyeglass frames press the X button. If not press the On/Off button. |
| 320 | Stage 20 of Program Algorithm:<br>Pressing the X Button 67 at the end of Voice Command Number 19 takes the user to Voice Command Number 28.<br>Pressing the On/Off Button 68 at the end of Voice Command Number 19 takes the user to Voice Command Number 27. |
| 220 | Voice Command Number 20:<br>Look into the eyehole that is flashing. |
| 321 | Stage 21 of Program Algorithm:<br>After Voice Command Number 20 the user is taken to Voice Command Number 22. |
| 221 | Voice Command Number 21:<br>Now look into the other eyehole that is flashing. |
| 322 | Stage 22 of Program Algorithm:<br>After Voice Command Number 21 the user is taken to Voice Command Number 22. |
| 222 | Voice Command Number 22:<br>Close your other eye and focus on the lowest line you can read. Try not to tilt your head left or right. Now start pressing the down button to see if it improves your vision.<br>You may press the up button to go in the other direction. Keep making adjustments until you can read the lowest line that you can. Take your time.<br>After you find the lowest line that you can read, press the X button. |
| 323 | Stage 23 of Program Algorithm:<br>The Up and Down Buttons 71 and 73 make −/+0.25D changes respectively to the Spherical Component during Voice Command Number 22.<br>Pressing the X Button 67 after Voice Command Number 22 saves refractive measurements for Add 2 under the appropriate eye label on Display Screen 77, FIG. 17.<br>The user is then taken to Voice Command Number 23. |
| 223 | Voice Command Number 23:<br>If you would like glasses for reading at computer monitor distance press the up button. If you do not want glasses for computer monitor distance press the X button. |
| 324 | Stage 24 of Program Algorithm:<br>Pressing the Up Button 71 at the end of Voice Command Number 23 changes the Spherical Component by (−) 0.25D and sets the system up for the Add 3 Near Vision Test FIG. 9C (other embodiments may suffice for this stage of near vision testing as depicted in FIG. 13C for example). The user is then taken to Voice Command Number 25.<br>Pressing X Button 67 at the end of Voice Command Number 23 takes the user to Voice Command Number 24. |
| 224 | Voice Command Number 24:<br>If you would like glasses for very close work such as fly tying, sewing, or soldering press the down button. If you do not want glasses for very close working vision move the test switch to the other side. |
| 325 | Stage 25 of Program Algorithm:<br>Moving Test Switch 69 to the other side at the end Voice Command Number 24, takes the user to Voice Command Number 21, unless this is the second eye tested, in which case the user is taken to Voice Command Number 19. The appropriate eyepiece light 17 or 18 will start flash for a few seconds if user was taken to Voice Command Number 21.<br>Pressing the Down button 73 at the end of Voice Command Number 24 adds (+) 0.25D to the Spherical Component and takes the user to Voice Command Number 26. |
| 225 | Voice Command Number 25:<br>Keep pressing the up button and down button as needed until you can read the print most clearly. When finished press the X button. |
| 326 | Stage 26 of Program Algorithm:<br>Pressing the X Button at the end of Voice Command Number 25 saves refractive measurements for Add 3 under the appropriate eye label on Display Screen 77, FIG. 17.<br>The user is then taken to Voice Command Number 24. |
| 226 | Voice Command Number 26:<br>Keep pressing the down button and if needed the up button until you can read the print most clearly. When finished move the test switch to the other side. |
| 327 | Stage 27 of Program Algorithm:<br>Moving Test Switch 69 to the other side at the end of Voice Command Number 26 saves refractive measurements for Add 1 under the appropriate eye label on the Display Screen 77, FIG. 17.<br>The user is then taken to Voice Command Number 21, unless this was the second eye tested, in which case the user is taken to Voice Command Number 19. The appropriate eyepiece light 17 or 18 will flash for a few seconds if the user is taken to Voice Command Number 21. |

TABLE 1-continued

227 Voice Command Number 27:
    Thank you for using Vipassana. Your eye measurements will print shortly.
328 Stage 28 of Program Algorithm:
    Data on Display Screen 77, FIG. 17 are printed during Voice Command Number
    27. The device then shuts off.
228 Voice Command Number 28:
    Place your forehead against the headrest and don't move it. Now close one eye.
    You will use the Left and Right Buttons to move a needle so that it points to the
    exact center of your pupil. Your pupil is the black circle in the center of your eye,
    which is reflected in the mirror. When finished press the X button.
329 Stage 29 of Program Algorithm:
    Pressing Left Button 74 during Voice Command Number 28 moves PD Needle
    98 to the left via PD Motorized Ball Screw 96 riding on PD Ball Screw Guide
    Rail 97. Pressing Right Button 72 moves PD Needle 98 in the other direction
    using the same system. Pressing X Button 67 causes device to store the position
    of PD Needle 98 along PD Ball Screw Guide Rail 97 for future calculation. The
    user is then taken to Voice Command Number 29.
229 Voice Command Number 29:
    Now open your other eye and close the eye you just tested. Use the Left and Right
    Buttons again to move the needle to the exact center of your pupil. When finished
    press the X button.
330 Stage 30 of Program Algorithm:
    Pressing X Button 67 at the end of Voice Command Number 29 causes Operating
    Unit and Processor 43 to note the position of PD Needle 98 along the PD Ball
    Screw Guide Rail 97 and calculate the distance in millimeters between this
    current position and the stored positional data of PD Needle 98 from Stage 29 of
    Program Algorithm. This number represents the user's PD, which is then
    displayed on Display Screen 77, FIG. 17. The user is then taken to Voice
    Command Number 27.

Figure 22:
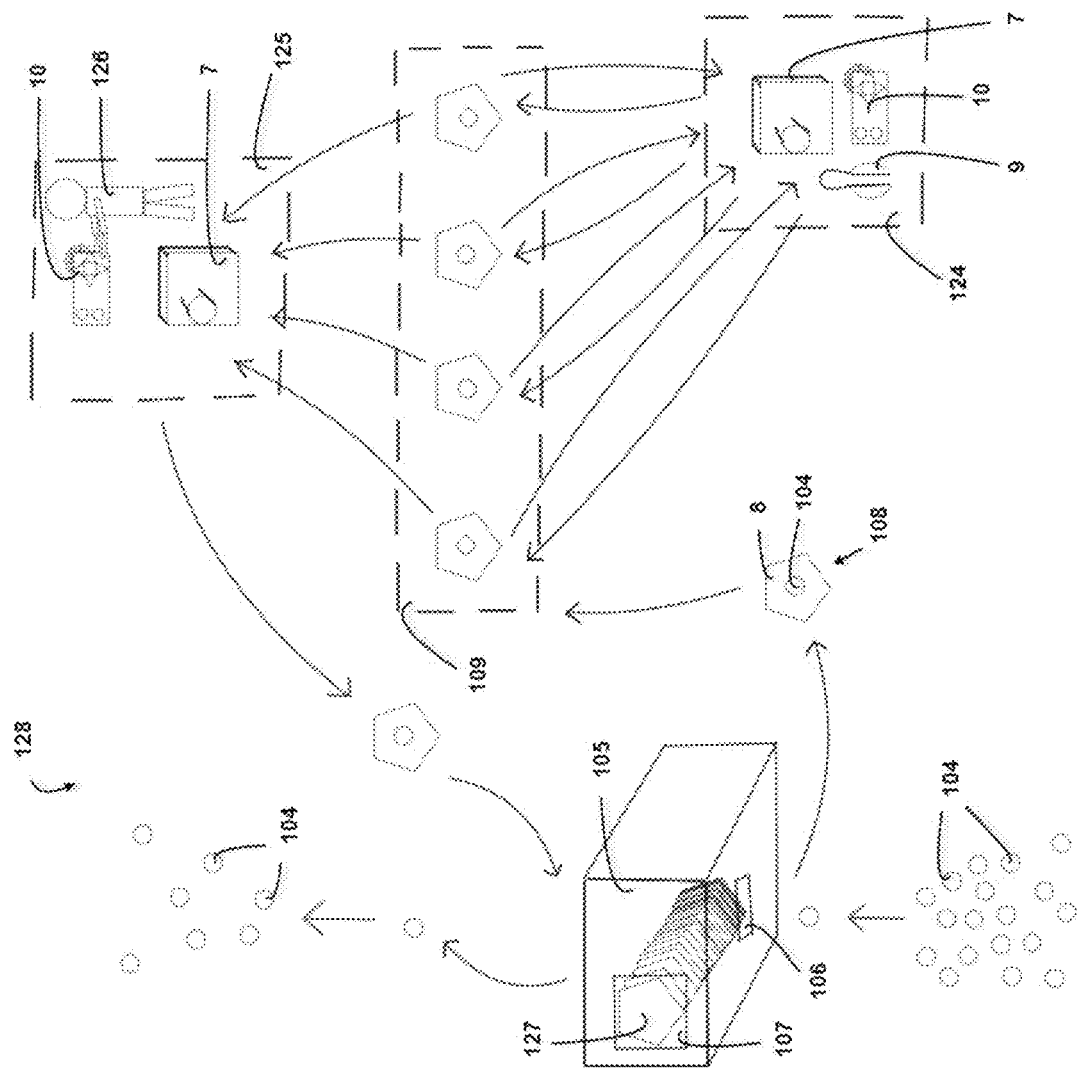
FIG. 22 illustrates a system for employing multiple refractions that are facilitated by an eye care professional

FIG. 22 illustrates a system 127 for employing multiple refractions that are facilitated by an eye care professional. The system 127 may comprise a fob 8, a fob receptacle 105, a queue 109, a SSR station 124 and an eye care professional station 125. Fob 8 is a contactless, proximity device that may communicate wirelessly with a refractor 7 when in its proximity. Fob 8 may receive data from a refractor 7, store that data, and then transfer that data to another refractor 7. Together, a fob 8 and a refractor 7 may provide paging capabilities to improve patient flow in an office based setting by signaling patients to move from a queue 109 to an eye care professional station 125 or a SSR station 124 at the appropriates times. The fob receptacle 105 may be used to keep the fobs in order which ensures that each patient is paged to complete SSR, as appropriate.

In this particular embodiment of a system 127, efficiency is improved when patients 104 grab their own fob 8 from a stack of fobs 127 via a dispensing end 106 of a fob receptacle 105, thereby becoming a patient-fob pair 108. Multiple patient-fob pairs 108 enter a queue 109, whereby each patient 104 waits for a page from their fob 8 to engage in SSR. Next, a refractor 7 at SSR station 124 sends a page to the next patient-fob pair 108 waiting in line at queue 109. The fob 8 signals the patient via any number of sensory cues, to move to SSR station 124, where they undergo the SSR process. In some cases, the fob is configured to convert an alert into a sensory cue and/or message that is picked up by the user. At the end of the SSR process, a refractor 7 sends the refractive measurements to the patient's fob 8 for storage and later use. The patient-fob pair 108 moves back to the queue 109 to await a second page. Next, a refractor 7 at eye care professional station 125 sends a page to the next patient-fob pair 108 waiting in the queue. The fob signals the patient to move to eye care professional station 125. Once the patient-fob pair 108 is in close proximity of the refractor 7, the fob 8 transmits the refractive measurements to refractor 7 directly, through a local area network, by wireless peer-to-peer means, or the internet. The refractor 7 automatically manipulates its trial lenses to correct for the patient's refractive error based on the custom refractive measurements saved on the fob from the SSR process. An eye care professional 126 uses a control unit 10 to make any beneficial changes to the trial lenses prior to preparing a prescription. Finally, the patient-fob pair 108 moves to a fob receptacle 105. The patient places their fob on the stack of fobs 127 through an opening 107 of the fob receptacle 105. The patient then leaves with their prescription.

The functions of a fob 8 are not limited to a fob and may be replaced with a web based application, a smartphone or tablet device, and the like.

System 127 may be set up in many ways. For example the eye care professional may control a refractor from a remote location using telemedicine technology. There may be many versions of SSR stations, eye care professional stations and fob receptacles.

Figure 23:
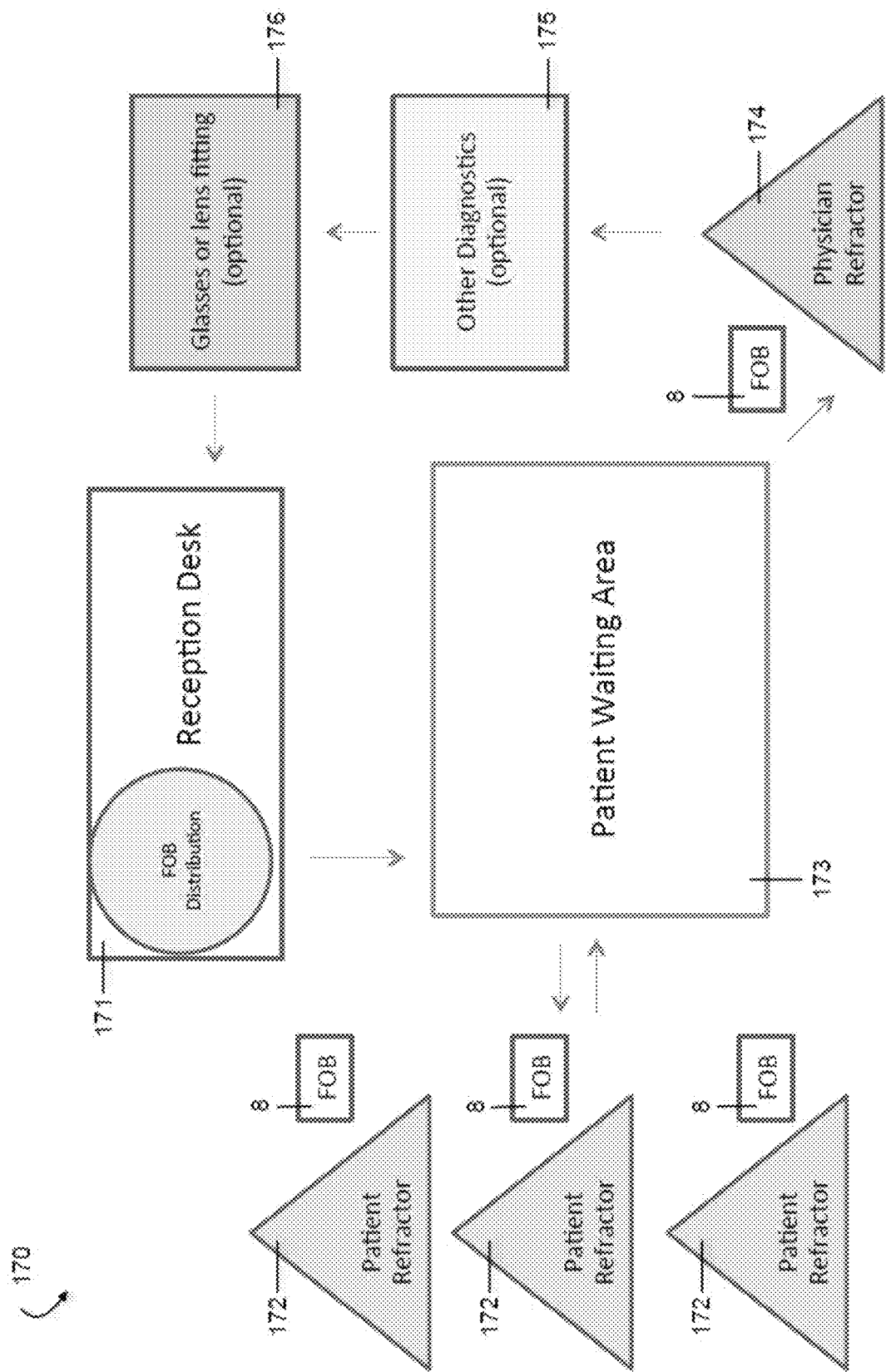
FIG. 23 illustrates a method for using the fob device in accordance with some embodiments of the invention.

FIG. 23 illustrates a method for using a fob device 8 in accordance with some embodiments of the invention. A fob device that may be combined with the SSR process for the purpose of increasing the efficiency and patient flow when an eye care professional is doing refractions on a large scale in accordance with some embodiments of the invention. System 170 may comprise a reception desk with FOB distribution area 171, multiple FOBs 8, multiple patient refractors 172, a patient waiting area 173, a physician refractor 174, other diagnostics 175, and eye wear fitting area 176. Patients are assigned a FOB 8 at the reception desk 171. The patient and FOB 8 then enter patient waiting area 173. When a patient refractor 172 becomes available, the patient refractor 172 pages the next patient in line via their FOB 8. After being alerted by FOB 8, the patient is signaled to use the available patient refractor 172. The patient then utilizes automated SSR system 169. Upon completion of the automated SSR process, the patient refractor 172 wirelessly sends the SSR measurements to the patient's FOB 8 and is signaled back to the patient waiting area 173. When the physician refractor 174 becomes available, the physician refractor 174 pages the next patient in line via their FOB 8. After being alerted by FOB 8, the patient is signaled to physician refractor 174. Once the patient and their FOB 8 reach the physician refractor 174, the FOB 8 automatically and wirelessly sends the SSR measurements to the physician refractor 174, which automatically places the corrected lenses in the optical path of the patient based on the SSR measurement data. An eye care professional may make any needed changes to the refractive measurements and run further tests. Next, the patient and FOB 8 are signaled to other diagnostics 175 for more testing if appropriate, then to eye wear fitting 176 if appropriate, and then to the reception desk 171 to drop off the FOB 8 and check out. The FOB 8 is able to also communicate wirelessly with any office based electronic medical records and update the records as needed during the office visit. FOB 8 may also be replaced with a smartphone app that uses contactless technology for communication, such as those used by POS machines (e.g. apple pay).

Figure 24:
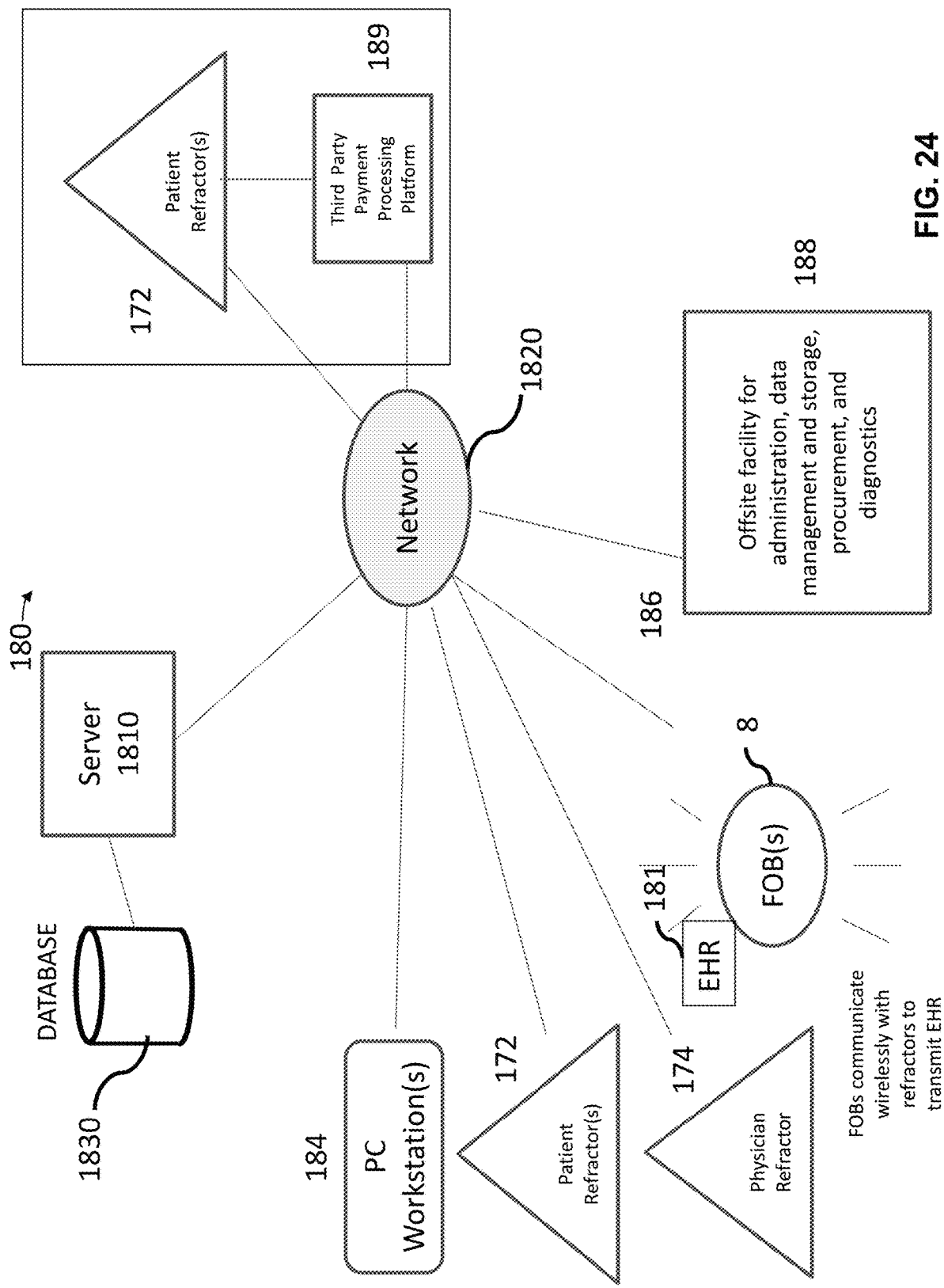
FIG. 24 is a network diagram employing SSR in accordance with some embodiments of the invention.

FIG. 24 is a network diagram of system 180 in accordance with some embodiments of the invention. System 180 may comprise a server 1810, a plurality of refractor devices 172,174, one or more media transportation devices (e.g., fob 8), a network 1820, an offsite facility 188 and optional computing devices 184. Each of the components 172,174, 184, 1810 and 188 may be operatively connected to one another via network 1820 or any type of communication links that allows transmission of data from one component to another.

In the embodiment of FIG. 24, two-way data transfer capability may be provided between the server and each refractor device. The refractor devices can also communicate with one another via the server (i.e., using a client-server architecture). In some embodiments, the refractor devices can communicate directly with one another via a peer-to-peer communication channel. The peer-to-peer communication channel can help to reduce workload on the server by utilizing resources (e.g., bandwidth, storage space, and/or processing power) of the refractor devices.

The components may be located in any locations. The server 1810 may or may not be located remote to the one or more refractor devices. The patient refractors and physician refractors may or may not be located in the same location. The offsite facility 188 may or may not be located with the one or more refractor devices or the server.

A server may comprise one or more server computers configured to perform one or more operations consistent with disclosed embodiments. In one aspect, a server may be implemented as a single computer, through which a refractor device is able to communicate with other components of the network layout. In some embodiments, a refractor device may communicate with the server through the network. In some embodiments, the server may embody the functionality of one or more SSR systems or methods. In some embodiments, the SSR systems may be implemented inside and/or outside of the server. For example, the SSR systems may be implemented by software and/or hardware components included with the server or remote from the server.

In some embodiments, a refractor device may be directly connected to the server through a separate link (not shown in FIG. 24). In certain embodiments, the server may be configured to operate as a front-end device configured to provide access to one or more SSR system(s) consistent with certain disclosed embodiments. The server may, in some embodiments, utilize the SSR system(s) to process input data from a refractor device in order to generate next voice command, test results and the like. The server may be configured to store the users' data in the database. The server may also be configured to search, retrieve, and analyze (compare) user data and test result or prescription data stored in the database. In some cases, the data and information may include a user's previous vision related data obtained with or without an SSR system.

A server may include a web server, an enterprise server, or any other type of computer server, and can be computer programmed to accept requests (e.g., HTTP, or other protocols that can initiate data transmission) from a computing device (e.g., a user device) and to serve the computing device with requested data. In addition, a server can be a broadcasting facility, such as free-to-air, cable, satellite, and other broadcasting facility, for distributing data. A server may also be a server in a data network (e.g., a cloud computing network).

A server may include known computing components, such as one or more processors, one or more memory devices storing software instructions executed by the processor(s), and data. A server can have one or more processors and at least one memory for storing program instructions. The processor(s) can be a single or multiple microprocessors, field programmable gate arrays (FPGAs), or digital signal processors (DSPs) capable of executing particular sets of instructions. Computer-readable instructions can be stored on a tangible non-transitory computer-readable medium, such as a flexible disk, a hard disk, a CD-ROM (compact disk-read only memory), and MO (magneto-optical), a DVD-ROM (digital versatile disk-read only memory), a DVD RAM (digital versatile disk-random access memory), or a semiconductor memory. Alternatively, the methods disclosed herein can be implemented in hardware components or combinations of hardware and software such as, for example, ASICs, special purpose computers, or general purpose computers. While FIG. 24 illustrates the server as a single server, in some embodiments, multiple devices may implement the functionality associated with the server.

The network may be configured to provide communication between various components of the network layout depicted in FIG. 24. The network may be implemented, in some embodiments, as one or more networks that connect devices and/or components in the network layout for allowing communication between them. For example, as one of ordinary skill in the art will recognize, the network may be implemented as the Internet, a wireless network, a wired network, a local area network (LAN), a Wide Area Network (WANs), Bluetooth, Near Field Communication (NFC), or any other type of network that provides communications between one or more components of the network layout. In some embodiments, the network may be implemented using cell and/or pager networks, satellite, licensed radio, or a combination of licensed and unlicensed radio. The network may be wireless, wired, or a combination thereof.

The SSR system(s) may be implemented as one or more computers storing instructions that, when executed by one or more processor(s), generate a series of command to guide a user in an SSR process, in response to a user input automatically generate instructions to adjust lenses and components of the SSR system to perform one or more operations consistent with disclosed embodiments. The SSR system(s) may further store data generated during the SSR process such as vision test result, prescription and the like. In some embodiments, the server may be the computer in which the SSR system(s) are implemented.

The server may access and execute the SSR system(s) to perform one or more processes consistent with the disclosed embodiments. In certain configurations, the SSR system(s) may be software stored in memory accessible by the server (e.g., in a memory local to the server or remote memory accessible over a communication link, such as the network). Thus, in certain aspects, the SSR system(s) may be implemented as one or more computers, as software stored on a memory device accessible by the server, or a combination thereof. For example, one SSR system may be computer hardware executing one or more SSR components such as the controller for generating instructions to the refractor, and another SSR system may be software that, when executed by the server, performs one or more SSR processes such as generating voice command and interacting with a user.

The refractor devices, the server, and the other component(s) may be connected or interconnected to one or more database(s) 1830. The database(s) may be one or more memory devices configured to store data (e.g., computer commands, instructions, user test result, health records, etc.). Additionally, the database(s) may also, in some embodiments, be implemented as a computer system with a storage device. In one aspect, the database(s) may be used by components of the network layout to perform one or more operations consistent with the disclosed embodiments. In certain embodiments, one or more the database(s) may be co-located with the server, or may be co-located with one another on the network. One of ordinary skill will recognize that the disclosed embodiments are not limited to the configuration and/or arrangement of the database(s).

Any of the refractor devices, the server, the database(s), and/or the offsite facility system(s) may, in some embodiments, be implemented as a computer system. Additionally, while the network is shown in FIG. 24 as a "central" point for communications between components of the network layout, the disclosed embodiments are not limited thereto. For example, one or more components of the network layout may be interconnected in a variety of ways, and may in some embodiments be directly connected to, co-located with, or remote from one another, as one of ordinary skill will appreciate. Additionally, while some disclosed embodiments may be implemented on the server, the disclosed embodiments are not so limited. For instance, in some embodiments, other devices (such as one or more user devices) may be configured to perform one or more of the processes and functionalities consistent with the disclosed embodiments, including embodiments described with respect to the server and the SSR system.

In an example, a server 182 may be located in an office based location 178, connected through a HUB to a router in a local area network (LAN) which wirelessly transmits data. The router is connected to the internet through a firewall. Within the network are one or more patient or physician refractors 174, 175 which communicate wirelessly with FOBs 8 to transmit electronic health records (EHR) 181. The electronic health records (EHR) 181 are transmitted to FOB(s) 8 and physician refractor 174 wirelessly in any network setting. The EHR 181 may also be transmitted to or from patient refractor(s) 172 at any satellite location(s). This system will also allow for appointment booking, updating a patient's refractive measurements, ordering glasses, or other health-related necessities through the network.

In another example, all devices may interface with a Personal Computer (PC) workstation 184 through the wireless network in an office based setting, or even a satellite location which coordinates workflows or stores data on a server 182. The office-based location(s) may utilize automated SSR system 169 and/or high throughput office based refraction system 170. The satellite location(s) utilize automated SSR system 169 and may be used with or without an appointment by patients or non-patients. The satellite location(s) provides the general public with 24-hour access to the automated SSR system 169, allows eye care professionals to advertise and book appointments, and allows patients and eye care professionals to interface remotely with an audio-video feed via the Internet 1820. Satellite locations may be housed in retail stores or centers, or other high foot traffic areas. Since satellite locations will generally be unmanned in many embodiments, payment may be taken through a third party payment processing platform (189), such as Square Pay, Apple Pay, Samsung pay, PayPal, and the like. The FOB(s) 8 may also be taken with users to each satellite location for the purpose of wirelessly auto-transmitting previous refractive measurements in order for the patient refractor 172 to automatically place the correct refractive lenses in the user's optical path. Data may also be saved on the FOB(s) 8 for later use at office-based locations. Alternatively, other devices such as a user device (e.g., smart phones, cell phones, personal digital assistants (PDAs), tablets and other portable devices, smartwatches and other wearable devices) may be used for storing and transmitting the data among the office based or satellite locations. FOB 8 in office based, or satellite locations. EHR 181 information may also be distributed via an email platform.

In some cases, given the critical nature of EHR 181, network complexities, requirements for user interface, needed software updates, and patient—physician interface, it may be appropriate to establish an offsite administrative facility 188, or headquarters in a remote location for data management, and storage, system and network administration, procurement, and diagnostics. In some embodiments, this facility will interface with an office based location through a firewall, or a satellite location through a virtual private network (VPN) 1820. Other security measures may also be taken to secure the network and preserve EHR 181.

It is to be understood that the above description is intended to be illustrative and not restrictive. Therefore, the scope of the invention should be determined not with reference to the above description, but instead should be determined with reference to the appended claims along with full scope of their equivalents.

While preferred embodiments of the invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A system for automated vision measurements comprising:
   a lens chamber comprising a plurality of prearranged corrective lenses;
   one or more eyepieces fitted to the chamber;
   a sun and planet gear system, wherein at least one corrective lens of the plurality of corrective lenses is mounted within the sun and planet gear system;
   at least one digital acuity monitor, wherein a corrective lenses-to-digital acuity monitor distance is adjustable and further wherein all or parts of the image on the digital acuity monitor is operable to be adjusted;
   an input device for adjusting the digital acuity monitor and the plurality of corrective lenses;

an audio device;
a vision measurement computer comprising a memory, a processor, and a plurality of programming instructions, the plurality of programming instructions stored in the memory that when executed by the processor cause the processor to:
provide audio instructions, via the audio device;
provide visual instructions via the digital acuity monitor;
iteratively:
   receive adjustments for the plurality of corrective lenses,
   receive adjustments of the image on the digital acuity monitor,
   receive adjustments of the corrective lenses-to-digital acuity monitor distance;
   provide audio to the audio device, based on the corrective lenses-to digital acuity monitor distance;
   change position of, at least, the plurality of corrective lenses between assessments of spherical error, cylindrical error and cylindrical axis error;
   change position of the image on the digital acuity monitor, and corrective lenses-to digital acuity monitor distance;
   adjusting spherical power to keep a circle of least confusion focused on a retina;
wherein the input device has a fine-tuning mechanism for continuously rotating a cylindrical axis to find a user's axis of astigmatism, without the use of a cross cylinder examination;
   receive a selection from the input device, the selection setting a final position of the plurality of corrective lenses;
providing one or more vision measurements comprising, at least, a spherical or cylindrical measurement, or both.

2. The system of claim 1, wherein the eyepiece is operable to automate the measurement of a vertex distance.

3. The system of claim 1, wherein an image of a user's pupils and a movable indicator, controlled by the input device, measures a user's pupillary distance.

4. The system of claim 3, further comprising a proximity device operable to automatically store refractive measurements and transmit instructions to arrange, by the vision measurement computer, the plurality of lenses based on stored refractive measurements, when the proximity device is in proximity of the lens chamber.

5. The system of claim 4, wherein the vision measurement computer is operable to hold constant the cylindrical axis while changing a cylindrical power and hold constant the cylindrical power while changing the cylindrical axis.

6. The system of claim 5, wherein one or more test images are placed at one or more distances from the user.

7. The system of claim 6, wherein spherical, cylindrical and axis measurements are made, the vision measurement computer, at the one or more distances.

8. The system of claim 7, wherein the accuracy of the spherical, cylindrical and axis measurements are verified, by the vision measurement computer, based on the percentage of characters the user orients, using the input device, on a video acuity monitor to exactly match the orientation of other characters on the video acuity monitor.

9. The system of claim 8, further comprising measuring, by the vision measurement computer, a vertex distance.

10. The system of claim 9, further comprising measuring, by the vision measurement computer, a pupillary distance.

11. The system of claim 10, wherein measurements of spherical error, cylindrical error, axis error, vertex distance and or pupillary distance are provided to the user via the audio device or the video acuity monitor, or both.

12. The system of claim 11, wherein the vision measurement computer is further operable to store the measurements to the proximity device.

13. The system of claim 12, wherein the proximity device is further operable to transmit the measurements to the vision measurement computer, when the proximity device is in proximity of the one or more lens chambers.

14. The system of claim 13, wherein the vision measurement computer is further operable to change position of the plurality of corrective lenses based on the refractive measurements.

15. The system of claim 14, wherein the proximity device is further operable to send sensory alerts.

16. The system of claim 1, wherein a automated vision measurement system comprises a plurality of lens chambers.

17. The system of claim 1, wherein spherical refractive measurements are extrapolated for one or more near vision measurements.

\* \* \* \* \*